(12) United States Patent
Stoessel et al.

(10) Patent No.: US 7,683,229 B2
(45) Date of Patent: Mar. 23, 2010

(54) ORGANIC ELECTROLUMINESCENT DEVICE

(75) Inventors: Philipp Stoessel, Frankfurt Am Main (DE); Esther Breuning, Niedernhausen (DE); Liliana Bagala' Rampazzo, Rome (IT); Giulia Fioravanti, Rome (IT); Leonardo Mattiello, Rome (IT)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 11/632,568

(22) PCT Filed: Jul. 15, 2005

(86) PCT No.: PCT/EP2005/007745

§ 371 (c)(1),
(2), (4) Date: Jan. 7, 2008

(87) PCT Pub. No.: WO2006/005626

PCT Pub. Date: Jan. 19, 2006

(65) Prior Publication Data

US 2008/0093980 A1 Apr. 24, 2008

(30) Foreign Application Priority Data

Jul. 15, 2004  (IT)  .................. RM2004A0352

(51) Int. Cl.
*C07C 15/12* (2006.01)
*C07C 211/00* (2006.01)
*C07C 22/00* (2006.01)
*C07C 49/115* (2006.01)
*C07C 205/00* (2006.01)
*C07C 255/00* (2006.01)
*C07F 5/02* (2006.01)
*C07F 9/02* (2006.01)
*C07F 7/08* (2006.01)
*H01J 1/62* (2006.01)

(52) U.S. Cl. .................. 585/471; 585/360; 564/305; 564/427; 570/183; 568/1; 568/17; 568/326; 568/941; 428/917; 313/506; 558/411; 556/406

(58) Field of Classification Search ............... 585/360, 585/471; 558/411; 564/305, 427; 570/183; 556/406; 568/1, 17, 326, 941; 313/506; 428/917

See application file for complete search history.

(56) References Cited

FOREIGN PATENT DOCUMENTS

JP    2003261473    9/2003

OTHER PUBLICATIONS de Frutos et al., "*syn*-Trialkylated Truxenes: Building Blocks That Self-Associate by Arene Stacking", *Angew. Chem. Int. Ed.*, vol. 38, No. 1/2, pp. 204-207 (1999).
Ruiz et al., Overcrowded 5,10,15-Trisubstituted Derivatives: Synthesis of 5,10,15-Tri(fluorenylidiene)truxene, *Eur. J. Org. Chem.*, pp. 858-866 (2004).
Cao et al., "Extended π-Conjugated Dendrimers Based on Truxene", *J. Am. Chem. Soc.*, vol. 125, pp. 12430-12431 (Sep. 20, 2003).
Beilstein Database, Registry No. 2567499, Entry Date Jul. 5, 1989.
Beilstein Database, Registry No. 8463159, Entry Date May 16, 2000.
Beilstein Database, Registry No. 8469038, Entry Date May 16, 2000.
Beilstein Database, Registry No. 3463448, Entry Date Feb. 15, 1990.
Beilstein Database, Registry No. 6546975, Entry Date Apr. 18, 1994.
Beilstein Database, Registry No. 7731552, Entry Date Nov. 18, 1997.

*Primary Examiner*—Jafar Parsa
(74) *Attorney, Agent, or Firm*—Connolly Bove Lodge & Hutz LLP

(57) ABSTRACT

The present invention relates to novel truxene and isotruxene derivatives, in particular spirotruxene and spiroisotruxene derivatives, and to the use thereof in organic electronic devices, in particular organic electroluminescent devices.

22 Claims, No Drawings

ORGANIC ELECTROLUMINESCENT DEVICE

RELATED APPLICATIONS

This application is a national stage application (under 35 U.S.C. § 371) of PCT/EP2005/007745 filed Jul. 15, 2005, which claims the benefit of Italian application RM2004A000352 filed Jul. 15, 2004.

The use of organic semiconductors as functional materials in a number of different applications which can be ascribed to the electronics industry in the broadest sense has been reality for some time or is expected to become so in the near future. In the case of organic electroluminescent devices (OLEDs), the market introduction has already taken place. The general structure of devices of this type is described, for example, in U.S. Pat. No. 4,539,507, U.S. Pat. No. 5,151,629, EP 0676461 and WO 98/27136. However, these devices still exhibit considerable problems which require urgent improvement:

1. The operating lifetime is still short, in particular in the case of blue emission, meaning that it has to date only been possible to achieve simple applications commercially.
2. The compounds used are in some cases only sparingly soluble in common organic solvents, which makes their purification during the synthesis, but also the cleaning of the plants in the production of the organic electronic devices more difficult.
3. Some of the compounds used, which otherwise exhibit good properties in OLEDs, do not have a sufficiently high glass-transition temperature.

As the closest prior art, mention may be made of the use in fluorescent OLEDs of various condensed aromatic compounds, in particular anthracene or pyrene derivatives, as host materials, especially for blue-emitting electroluminescent devices, for example 9,10-bis(2-naphthyl)anthracene (U.S. Pat. No. 5,935,721). WO 03/095445 and CN 1362464 describe 9,10-bis(1-naphthyl)anthracene derivatives for use in OLEDs. Further anthracene derivatives which are suitable as host materials are described in WO 01/076323, in WO 01/021729, in WO 04/013073, in WO 04/018588, in WO 03/087023 or in WO 04/018587. Host materials based on aryl-substituted pyrenes and chrysenes are described in WO 04/016575, where corresponding anthracene and phenanthrene derivatives are also encompassed here in principle. Although good results have already been achieved with these compounds, it is necessary, for high-quality applications, to have improved host materials available.

The matrix material used in phosphorescent OLEDs is frequently 4,4'-bis(N-carbazolyl)biphenyl (CBP). The disadvantages are, inter alia, short lifetimes of the devices produced therewith and frequently high operating voltages, which result in low power efficiencies. In addition, CBP does not have a sufficiently high glass-transition temperature. Furthermore, it has been found that, for energetic reasons, CBP is unsuitable for blue-emitting electroluminescent devices, which results in poor efficiency. In addition, the structure of the devices is complex if CBP is used as matrix material since a hole-blocking layer and an electron-transport layer additionally have to be used. Improved triplet matrix materials based on keto compounds of spirobifluorene are described in WO 04/093207. For the best of the matrix materials described therein, however, toxic inorganic cyanides are required in the synthesis, meaning that the preparation of these materials is ecologically unacceptable.

The electron-transport compound used in organic electroluminescent devices is usually $AlQ_3$ (aluminium trishydroxyquinolate) (U.S. Pat. No. 4,539,507). This has a number of disadvantages: it cannot be vapour-deposited without leaving a residue since it partially decomposes at the sublimation temperature, which represents a major problem, in particular, for production plants. A further crucial practical disadvantage is the high hygroscopicity of $AlQ_3$, as is the low electron mobility, which results in higher voltages and thus in a lower power efficiency. In order to prevent short circuits in the display, it would be desirable to increase the layer thickness; this is not possible with $AlQ_3$ owing to the low charge-carrier mobility and the resultant increase in voltage. Furthermore, the inherent colour of $AlQ_3$ (yellow in the solid state), which can result in colour shifts, especially in the case of blue OLEDs, due to reabsorption and re-emission, has proven very unfavourable. It is only possible here to produce blue OLEDs having significant efficiency and colour location deficiencies. A further disadvantage of $AlQ_3$ is the instability to holes (Z. Popovic et al., *Proceedings of SPIE* 1999, 3797, 310-315), which can always result in problems on long-term use. In spite of the said disadvantages, $AlQ_3$ in OLEDs to date still represents the best compromise for the variety of requirements of an electron-transport material in OLEDs.

Thus, there continues to be a demand for improved materials, in particular host materials for blue-fluorescent emitters and host materials for triplet emitters, but also electron-transport materials which result in good efficiencies and at the same time in long lifetimes in organic electronic devices, give reproducible results in the production and operation of the device and are readily accessible synthetically. Likewise, there continues to be a need for improvement in other compounds used in OLEDs, such as hole-transport materials and fluorescent emitters.

Surprisingly, it has been found that compounds which contain certain novel truxene derivatives described below as skeleton have significant improvements over the prior art. These materials enable an increase in the efficiency and lifetime of the organic electronic device compared with materials in accordance with the prior art. Furthermore, these materials are highly suitable for use in organic electronic devices since they have a very high glass-transition temperature. The present invention therefore relates to these materials and to the use thereof in organic electronic devices. The skeleton of truxene and isotruxene and the numbering of the positions are depicted in the following scheme:

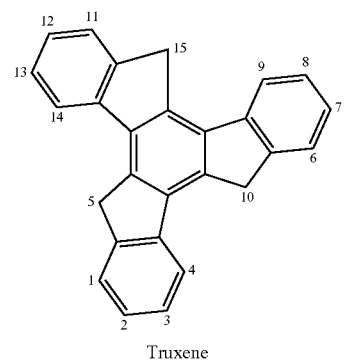

Truxene

-continued

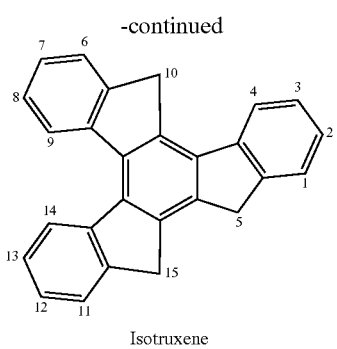

Isotruxene

The use of simple truxene derivatives for organic electronic devices is known in the literature (JP 2003/261473). However, these are less suitable owing to their low glass-transition temperature.

Furthermore, a later publication also describes the use of spirotruxene and an arylamino-substituted spirotruxene in organic light-emitting diodes (M. Kimura et al., *J. Mater. Chem.* 2005, 15, 2393-2398).

The invention relates to compounds of the formula (1) and formula (2)

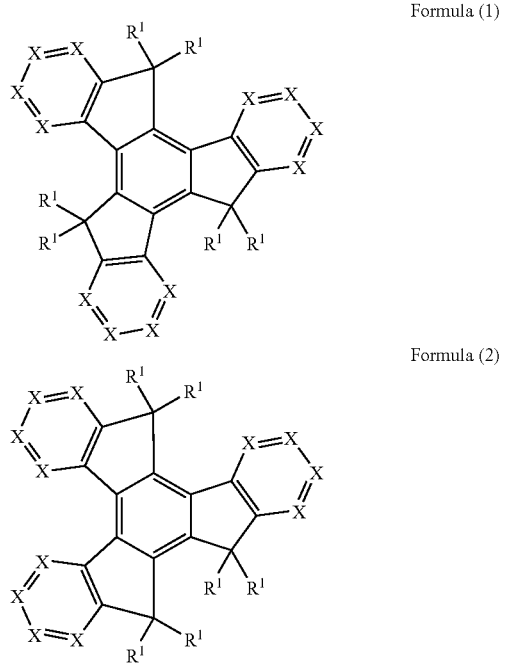

Formula (1)

Formula (2)

where the following applies to the symbols and indices used:
X is on each occurrence, identically or differently, CR or N;
R is on each occurrence, identically or differently, H, F, Cl, Br, I, CN, $NH_2$, $NO_2$, OH, $N(R^2)_2$, $Si(R^2)_3$, $B(OR^2)_2$, $B(OH)_2$, $Sn(R^2)_3$, $C(=O)R^2$, $P(R^2)_2$, $P(=O)(R^2)_2$, $S(=O)R^2$, $S(=O)_2R^2$, a straight-chain alkyl, alkoxy or thioalkoxy chain having 1 to 40 C atoms or a branched or cyclic alkyl, alkoxy or thioalkoxy chain having 3 to 40 C atoms, each of which may be substituted by $R^3$ and in which, in addition, one or more non-adjacent C atoms may be replaced by $N-R^3$, O, S, O—CO—O, CO—O, CO—$NR^3$, —$CR^3$=$CR^3$— or —C≡C— and in which, in addition, one or more H atoms may be replaced by F, Cl, Br, I or CN, or an aromatic or heteroaromatic ring system, which may also be substituted by one or more non-aromatic radicals R, or a combination of two, three or four of these systems; two or more radicals R here may also form a mono- or polycyclic, aliphatic, aromatic or heteroaromatic ring system with one another;

$R^1$ is on each occurrence, identically or differently, H, F, Cl, Br, I, CN, a straight-chain alkyl, alkoxy or thioalkoxy chain having 1 to 40 C atoms or a branched or cyclic alkyl, alkoxy or thioalkoxy chain having 3 to 40 C atoms, each of which may be substituted by $R^3$ and in which one or more non-adjacent C atoms may be replaced by $N-R^3$, O, S, O—CO—O, CO—O, CO—$NR^3$, —$CR^3$=$CR^3$— or —C≡C— and in which, in addition, one or more H atoms may be replaced by F, Cl, Br, I or CN, or an aromatic or heteroaromatic ring system, which may also be substituted by one or more radicals R, or a combination of two, three or four of these systems; two or more radicals $R^1$ here may also form a mono- or polycyclic, aliphatic, aromatic or heteroaromatic ring system with one another;

with the proviso that the two substituents $R^1$ in position 5 and/or the two substituents $R^1$ in position 10 and/or the two substituents $R^1$ in position 15 represent an aromatic or heteroaromatic ring system;

$R^2$ is on each occurrence, identically or differently, a straight-chain alkyl chain having 1 to 40 C atoms or a branched or cyclic alkyl chain having 3 to 40 C atoms, each of which may be substituted by $R^3$ and in which one or more non-adjacent C atoms may be replaced by $N-R^3$, O, S, O—CO—O, CO—O, CO—$NR^3$, —$CR^3$=$CR^3$— or —C≡C— and in which, in addition, one or more H atoms may be replaced by F, Cl, Br, I or CN, or an aromatic or heteroaromatic ring system, which may also be substituted by one or more non-aromatic radicals R, or a combination of two, three or four of these systems; two or more radicals $R^2$ here may also form a mono- or polycyclic, aliphatic, aromatic or heteroaromatic ring system with one another;

$R^3$ is on each occurrence, identically or differently, H or an aliphatic or aromatic hydrocarbon radical having 1 to 20 C atoms.

The invention furthermore relates to the compounds spirotruxene of the formula (Ia) and spiroisotruxene of the formula (2a) and derivatives and salts thereof:

Formula (1a)

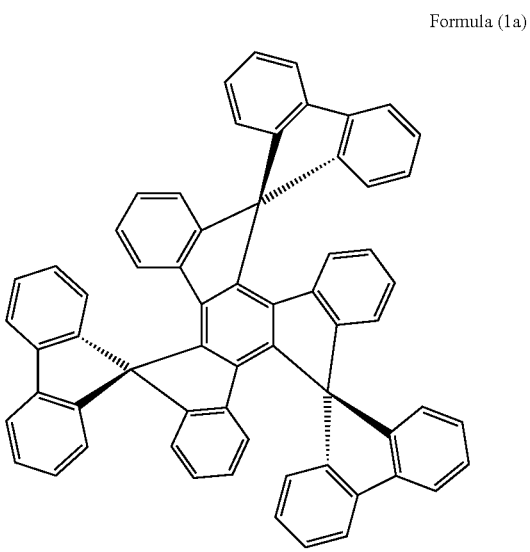

Formula (2a)

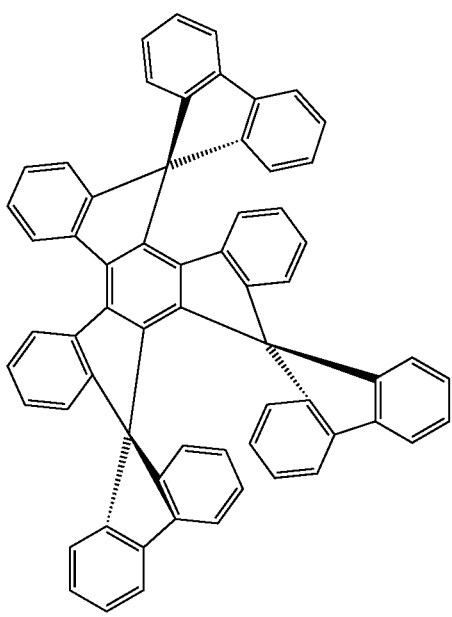

For the purposes of this invention, an aromatic ring system contains 6 to 80 C atoms in the ring system. For the purposes of this invention, a heteroaromatic ring system contains 2 to 80 C atoms and at least one heteroatom in the ring system, with the proviso that the total number of C atoms and heteroatoms in the ring system is at least 5. The heteroatoms are preferably selected from N, O and/or S. These ring systems may be substituted by one or more non-aromatic radicals R. For the purposes of this invention, an aromatic or heteroaromatic ring system is intended to be taken to mean a system which does not necessarily contain only aryl or heteroaryl groups, but in which a plurality of aryl or heteroaryl groups may also be interrupted by a short, non-aromatic unit (preferably less than 10% of the atoms other than H, particularly preferably less than 5% of the atoms other than H), such as, for example, an $sp^3$-hybridised C, N or O atom. A plurality of aryl or heteroaryl groups may likewise be interrupted by vinyl groups or acetylene groups. A plurality of aryl or heteroaryl groups may furthermore be interrupted by carbonyl groups, phosphine oxide groups, etc. Thus, for example, systems such as 9,9'-spirobifluorene, 9,9-diarylfluorene, triarylamine, diaryl ether, benzophenone, stilbene, tolan, etc., are also taken to mean aromatic ring systems for the purposes of this invention. The aromatic or heteroaromatic ring system or a part thereof may also be a condensed group here in the sense of the following definition.

For the purposes of this invention, a condensed aryl group is taken to mean a ring system having 10 to 60 aromatic ring atoms, a condensed heteroaryl group is taken to mean a ring system having 9 to 60 aromatic ring atoms, in each of which at least two aromatic or heteroaromatic rings are "fused" to one another, i.e. are condensed onto one another by anellation, i.e. have at least one common edge and a common aromatic π-electron system. These ring systems may be substituted by one or more non-aromatic radicals R or unsubstituted. Examples of condensed aromatic or heteroaromatic ring systems are naphthalene, benzothiophene, quinoline, isoquinoline, quinoxaline, anthracene, acridine, phenanthrene, phenanthroline, pyrene, naphthacene, perylene, chrysene, etc., while biphenyl, for example, does not represent a condensed aryl group since there is no common edge between the two ring systems therein. Fluorene or spirobifluorene likewise does not represent a condensed aromatic ring system for the purposes of this invention since the two phenyl units therein do not form a common aromatic electron system.

For the purposes of the present invention, a $C_1$- to $C_{40}$-alkyl group, in which individual H atoms or $CH_2$ groups may also be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A $C_1$- to $C_{40}$-alkoxy group is particularly preferably taken to mean methoxy, ethoxy, n-propoxy, i-propoxy, n-butoxy, i-butoxy, s-butoxy, t-butoxy or 2-methylbutoxy. An aromatic ring system having 6 to 80 C atoms or a heteroaromatic ring system having 2 to 80 C atoms, which may also in each case be substituted by the above-mentioned non-aromatic radicals R and which may be linked to the aromatic or heteroaromatic ring via any desired positions, is taken to mean, in particular, groups derived from benzene, naphthalene, anthracene, phenanthrene, pyrene, chrysene, perylene, fluoroanthene, naphthacene, pentacene, benzopyrene, biphenyl, biphenylene, terphenyl, terphenylene, fluorene, spirobifluorene, truxene, isotruxene, spirotruxene, spiroisotruxene, diphenyl ether, triphenylamine, dihydrophenanthrene, dihydropyrene, tetrahydropyrene, cis- or transindenofluorene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine or benzothiadiazole.

The compounds of the formula (1) or formula (2) preferably form glass-like films having a glass-transition temperature $T_g$ of greater than 100° C., particularly preferably greater than 130° C.

If the compound of the formula (1) or formula (2) is to be applied by a vapour-deposition process, its molecular weight is preferably less than 5000 g/mol, particularly preferably less than 2000 g/mol. It is preferably a compound having a defined constitution, where this may also be a mixture of different configurational isomers. If the compound is to be applied by a printing process or from solution, this restriction does not apply.

If the formation of a plurality of enantiomers or diastereomers is possible, each of these enantiomers or diastereomers and also mixtures of a plurality of these isomers are included in the invention.

Although this is evident from the description, it should again be emphasised here that a plurality of radicals R can form a ring system with one another and/or that a plurality of radicals $R^1$ can form a ring system with one another. It is preferred for a plurality of radicals $R^1$ to form a ring system with one another.

In a preferred embodiment of the invention, a maximum of one symbol X in each ring stands for N and the other symbols X in the same ring stand for CR. In a particularly preferred embodiment of the invention, the symbol X stands for CR.

In a further preferred embodiment of the invention, all radicals $R^1$ are aromatic or heteroaromatic ring systems, preferably having 5 to 30 aromatic ring atoms, particularly preferably having 6 to 18 aromatic ring atoms. These may each be substituted by R or unsubstituted. In a particularly preferred embodiment of the invention, $R^1$ on each occurrence, identically or differently, stands for a phenyl group which is substituted by R or unsubstituted.

In a further preferred embodiment, at least two radicals $R^1$ which are bonded to the same C atom each stand for a phenyl group which is substituted by R or unsubstituted and form a ring system with one another. In a particularly preferred embodiment of the invention, all radicals $R^1$ stand for a phenyl group which is substituted by R or unsubstituted and form a ring system with one another.

Very particular preference is given to compounds of the formula (3) or (4):

Formula (3)

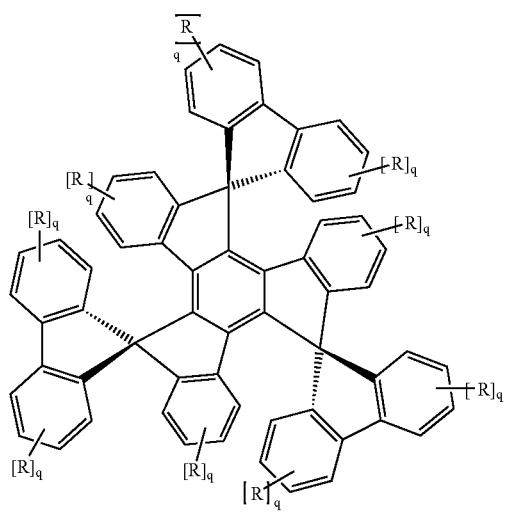

-continued

Formula (4)

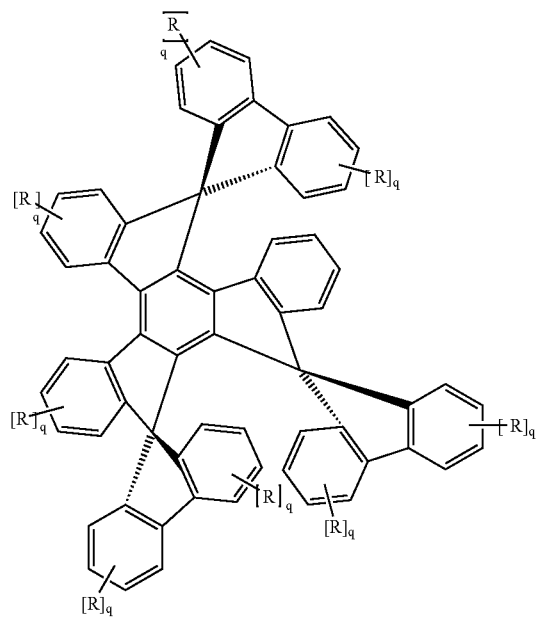

where the symbol R has the same meaning as described above, and q, identically or differently on each occurrence, denotes 0, 1, 2, 3 or 4, preferably 0, 1 or 2, particularly preferably 0 or 1.

The numbering of the spirotruxene and spiroisotruxene skeleton is shown in the following scheme:

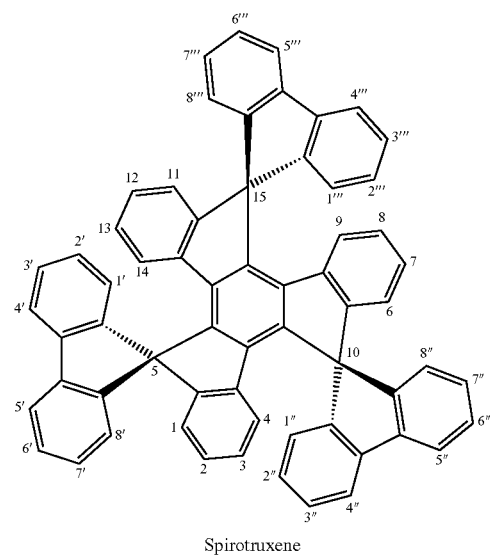

Spirotruxene

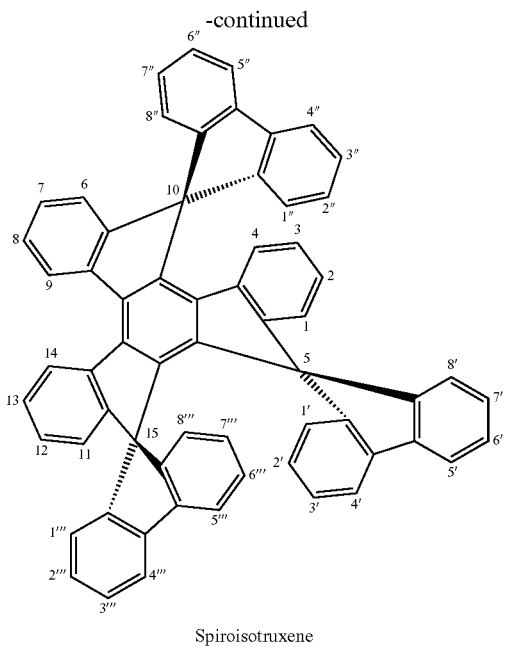

Spiroisotruxene

If the truxene or isotruxene skeleton in the formula (1) or (2) is substituted, these substituents are preferably bonded in positions 2, 7 and/or 12.

If the compounds of the formula (3) or (4) are substituted, the substituents are preferably bonded to the truxene or isotruxene skeleton in positions 2, 7 and/or 12 and/or in positions 2', 7', 2", 7", 2''' and/or 7''' of the spiro half of the molecule.

Preference is given to truxene and spirotruxene derivatives of the formulae (1) and (3).

Preference is furthermore given to symmetrically substituted compounds, in particular compounds which have a three-fold axis of rotation.

If present, preferred radicals R are on each occurrence, identically or differently, F, a straight-chain alkyl or alkoxy chain having 1 to 10 C atoms or a branched alkyl or alkoxy chain having 3 to 10 C atoms, each of which may be substituted by $R^3$ and in which one or more non-adjacent C atoms may be replaced by N—$R^3$, O, S, —$CR^3$=$CR^3$— or —C≡C— and in which, in addition, one or more H atoms may be replaced by F or CN, or an aromatic or heteroaromatic ring system having 5 to 30 aromatic ring atoms, which may also be substituted by one or more non-aromatic radicals R, or a combination of two or three of these systems; two or more radicals R here may also form a mono- or polycyclic, aliphatic or aromatic ring system with one another. If present, particularly preferred radicals R are on each occurrence, identically or differently, F, a straight-chain alkyl chain having 1 to 5 C atoms or a branched alkyl chain having 3 to 5 C atoms, in which, in addition, one or more non-adjacent C atoms may each be replaced by —$CR^3$=$CR^3$— or —C≡C— and in which, in addition, one or more H atoms may be replaced by F, or an aromatic or heteroaromatic ring system having 6 to 25 aromatic ring atoms, which may also be substituted by one or more non-aromatic radicals R, or a combination of two of these systems.

The precise choice of the radicals R depends on the desired function of the compound according to the invention. Preferred functions of the compounds according to the invention are as host material for fluorescent or phosphorescent emitters, as fluorescent dopant, as electron-transport material, as hole-blocking material or as hole-transport material.

For use as host material for fluorescent emitters, at least one radical R and/or $R^1$ in a preferred embodiment contains at least one aromatic ring system, in particular containing at least one condensed aryl or heteroaryl group, which may be substituted or unsubstituted. The condensed aryl or heteroaryl group is preferably bonded directly to the truxene or isotruxene skeleton or to the peripheral half of the spiro system of the spirotruxene or spiroisotruxene skeleton. It may be preferred here for further aromatic radicals to be bonded to the condensed aryl or heteroaryl group. It may likewise be preferred for more than one truxene or isotruxene group to be bonded to the condensed aryl or heteroaryl group. It may furthermore be preferred for a plurality of condensed aryl or heteroaryl groups to be bonded to the truxene or isotruxene skeleton. It is furthermore preferred, in particular for blue-emitting devices, for the host material to contain no double bonds, i.e. no stilbene structures, etc.

The condensed aryl or heteroaryl group particularly preferably contains two, three, four or five aromatic or heteroaromatic units, which are in each case condensed onto one another via one or more common edges and thus form a common aromatic system and which may be substituted or unsubstituted. The substitution may be appropriate in order to adjust the electronic properties or in order to obtain compounds with better solubility. The condensed aryl or heteroaryl group very particularly preferably contains three or four aromatic or heteroaromatic units, which are in each case condensed onto one another via one or more common edges and thus form a common aromatic system and which may be substituted or unsubstituted. The aromatic and heteroaromatic units condensed onto one another are very particularly preferably selected from benzene, pyridine, pyrimidine, pyrazine and pyridazine, each of which may be substituted or unsubstituted, in particular benzene and pyridine.

The condensed aryl or heteroaryl groups are particularly preferably selected from the group consisting of naphthalene, anthracene, acridine, phenanthrene, phenanthroline, pyrene, naphthacene, chrysene, pentacene and perylene, each of which may optionally be substituted. The condensed aromatic ring systems are very particularly preferably selected from the group consisting of anthracene, phenanthrene, pyrene and naphthacene, in particular anthracene, phenanthrene and pyrene, each of which may optionally be substituted.

The truxene or isotruxene here is preferably linked to the anthracene via the 1- or 9-position, in particular via the 9-position. The 10-position is then particularly preferably further substituted by an aromatic substituent or by a further truxene or isotruxene unit.

The truxene or isotruxene is preferably linked to the pyrene via the 1- or 2-position. The truxene or isotruxene is preferably linked to the pyrene via the 1,6-, 1,8-, 1,3- or 2,7-position if two truxene or isotruxene groups are present, particularly preferably via the 1,6- or 2,7-position. The truxene or isotruxene is preferably linked to the pyrene via the 1,3,6,8-position if four truxene or isotruxene groups are present. Furthermore, the pyrene may also be substituted by further, preferably aromatic substituents. The truxene or isotruxene is preferably linked to the phenanthrene via the 2-, 3- or 9-position if only one truxene or isotruxene group is present. The linking to the phenanthrene preferably takes place via the 2,7-, 3,6-, 2,9-, 2,10- or 9,10-position if two truxene or isotruxene groups are present, particularly preferably via the 2,7- or 3,6-position. Furthermore, the phenanthrene may also be substituted by further, preferably aromatic substituents.

The truxene or isotruxene is preferably linked to the perylene via the 3-position if only one group of this type is present. The linking to the perylene preferably takes place via the 3,4-, 3,9- or 3,10-position if two truxene or isotruxene groups are present, particularly preferably via the 3,9- or 3,10-position. The linking to the perylene preferably takes place via the 3,4,9,10-position if four truxene or isotruxene groups are present. Furthermore, the perylene may also be substituted by further, preferably aromatic substituents.

For reasons of clarity, the numbering of anthracene, phenanthrene, pyrene and perylene is shown below:

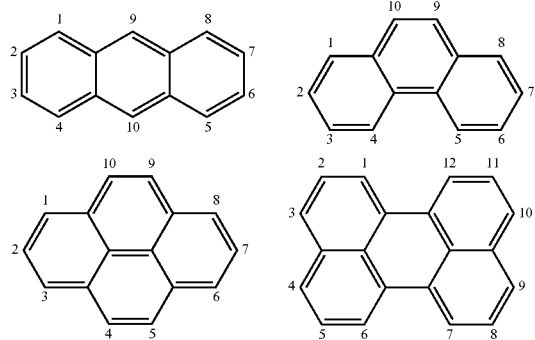

For use as host material for phosphorescent emitters, it is preferred that none of the substituents R and $R^1$ contains an aryl or heteroaryl group having more than 14 aromatic ring atoms, particularly preferably having more than 10 aromatic ring atoms. This does not exclude a plurality of aryl or heteroaryl groups of this type from being present in the substituent R or $R^1$, but excludes condensed aryl or heteroaryl groups having more than 14 aromatic ring atoms. It is furthermore preferred for the host material to contain no C=C double bonds, i.e. no stilbene structures, etc. In a further preferred embodiment, at least one substituent R is present which contains at least one carbonyl group, phosphine group, phosphine oxide group, thio group, sulfoxide or sulfone, which is particularly preferably bonded directly to the truxene or isotruxene skeleton or to the spiro half of the spirotruxene or spiroisotruxene. Very particularly preferred substituents R here are —C(=O)Ar, —P(Ar)$_2$, —P(=O)Ar$_2$, —SAr, —S(=O)Ar and —S(=O)$_2$Ar, where Ar stands for an aromatic or heteroaromatic ring system, preferably having 5 to 80 aromatic ring atoms, particularly preferably having 6 to 30 aromatic ring atoms, which contains no aryl or heteroaryl groups having more than 14 aromatic ring atoms, preferably none having more than 10 aromatic ring atoms; Ar is very particularly preferred selected from the group of aromatic ring systems consisting of benzene, naphthalene, pyridine, pyrimidine, pyrazine, pyridazine, quinoline, isoquinoline, quinoxaline, triazine, thiophene, benzothiophene, pyrrole, indole, furan, pyrazole, imidazole, triazole, oxadiazole, 2-biphenyl, 3-biphenyl, 4-biphenyl, fluorene, dihydrophenanthrene, spirobifluorene, truxene, isotruxene, spirotruxene, spiroisotruxene, terphenyl and binaphthyl, each of which may be substituted by non-aromatic radicals R, in particular benzene, 2-biphenyl, 3-biphenyl, 4-biphenyl, fluorene, dihydrophenanthrene, spirobifluorene, terphenyl, naphthyl or binaphthyl, each of which may be substituted by non-aromatic radicals R or unsubstituted.

For use as host material for phosphorescent OLEDs, at least one of the substituents R and $R^1$, preferably R, is furthermore preferably a substituted or unsubstituted carbazole radical.

For use as hole-transport material for fluorescent or phosphorescent organic electroluminescent devices or for other organic electronic devices, it is preferred for at least one substituent R or $R^1$ to contain at least one arylamine unit, diarylamine unit, carbazole unit, triarylamine unit, diarylphosphino unit, triarylphosphino unit and/or thiophene derivative. At least one substituent R particularly preferably contains at least one diarylamine unit, preferably bonded directly to the truxene or isotruxene skeleton, or a triarylamine unit, preferably bonded directly to the truxene or isotruxene skeleton. Particularly preferred substituents here are diphenylamine, carbazole, bis(paratolyl)amine, bis(parafluorophenyl)amine, triphenylamine, α- or β-naphthylphenylamine, α- or β-naphthyldiphenylamine or α- or β-dinaphthylamine, each of which may be substituted by one or more non-aromatic radicals R.

For use as hole-blocking material and/or as electron-transport material, it is preferred for at least one substituent R and/or $R^1$ to contain at least one electron-deficient heteroaryl group, particularly preferably selected from pyridine, pyridazine, pyrimidine, pyrazine, triazine, oxazole and oxadiazole. Preference is furthermore given for this function to materials in which at least one substituent R contains a carbonyl group, phosphine oxide group, sulfoxide group and/or sulfone group, each of which is particularly preferably bonded directly to the truxene or isotruxene skeleton or to the spiro half of the spirotruxene or spiroisotruxene. Very particularly preferred substituents R here are —C(=O)—Ar, —P(=O)Ar$_2$, —S(=O)Ar and —S(=O)$_2$Ar, where Ar stands for an aromatic or heteroaromatic ring system, preferably having 5 to 80 aromatic ring atoms, particularly preferably having 6 to 30 aromatic ring atoms. It is furthermore preferred for this function for at least one substituent R and/or $R^1$ to contain at least one substituted or unsubstituted oligophenylene group, preferably bonded directly to the truxene or isotruxene skeleton or to the spiro half of the spirotruxene or spiroisotruxene. The oligophenylene group here preferably contains 1, 2, 3 or 4 benzene units, particularly preferably 1 or 2 benzene units.

For use as fluorescent dopant for organic electroluminescent devices, it is preferred for at least one substituent R and/or $R^1$ to contain at least one vinylaryl unit, stilbene unit and/or tolan unit, particularly preferably at least one stilbene unit, where part of the stilbene unit may also form the truxene skeleton. The substituent R very particularly preferably contains at least one triarylamine unit in addition to the vinylaryl unit.

Examples of compounds of the formula (1) to formula (4) according to the invention are structures (1) to (70) depicted below. Which of the compounds depicted is particularly suitable for fluorescent devices and which for phosphorescent devices and which is also suitable for other uses is revealed in the above description.

(2)
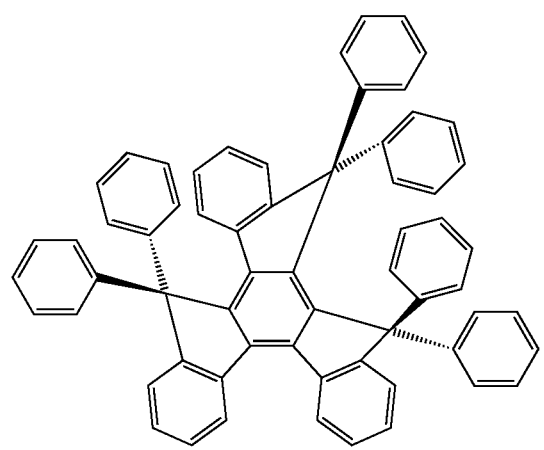
(1)
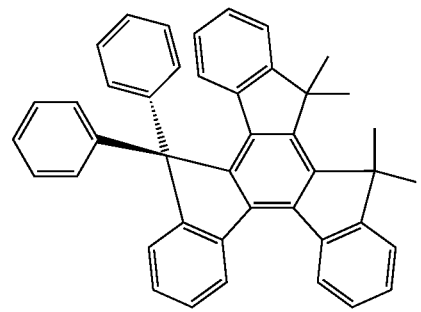
(4)
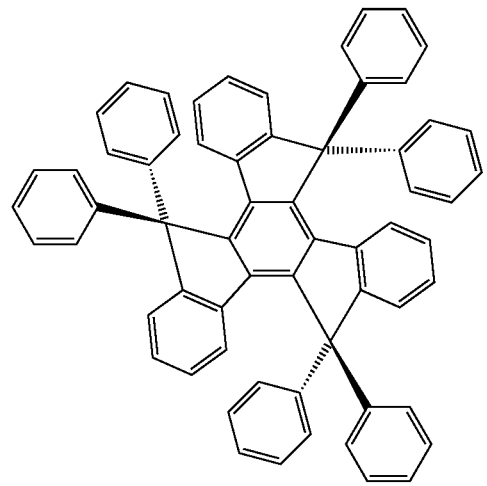
(3)
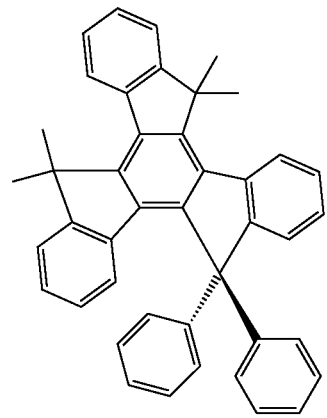

-continued
(6)
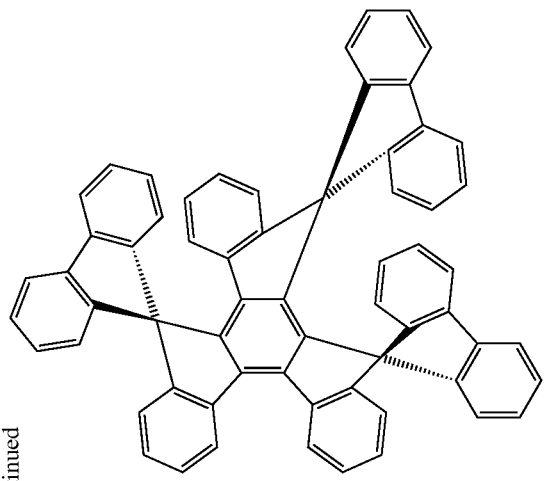
(8)
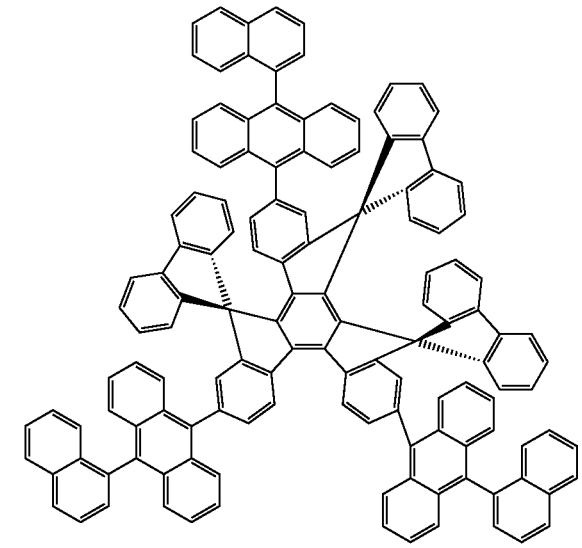
(7)
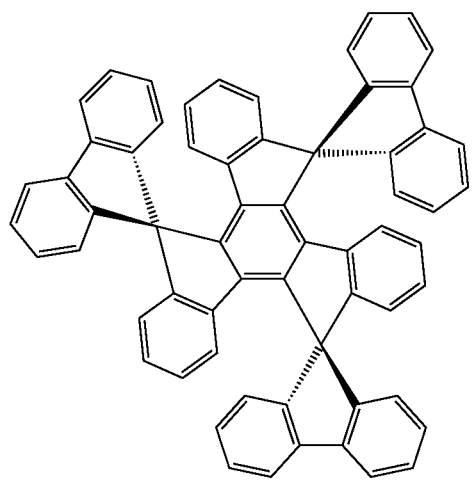
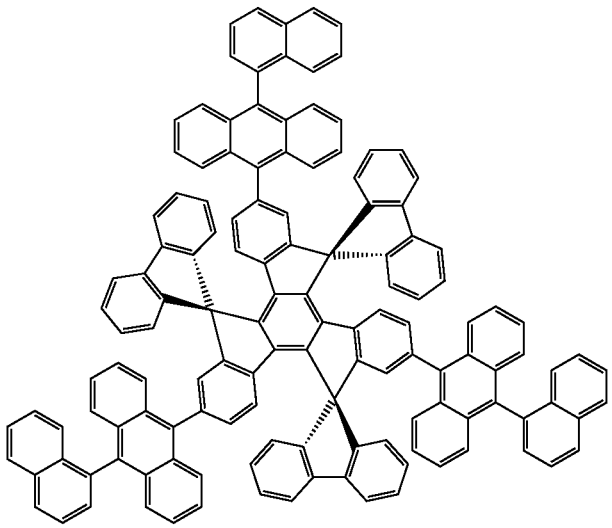

-continued
(10)
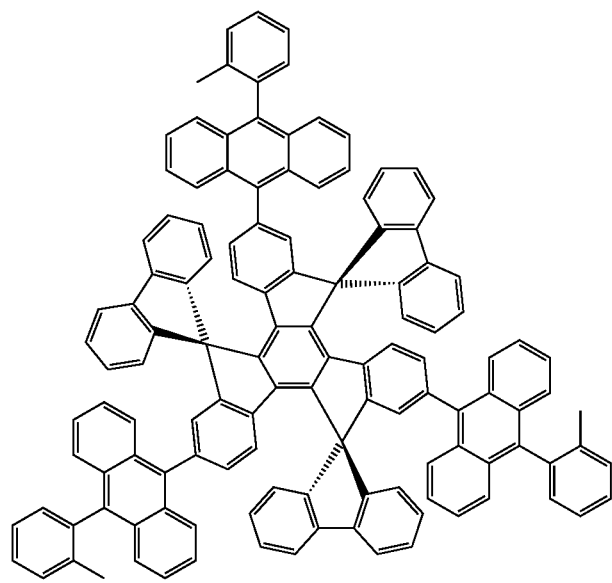
(9)
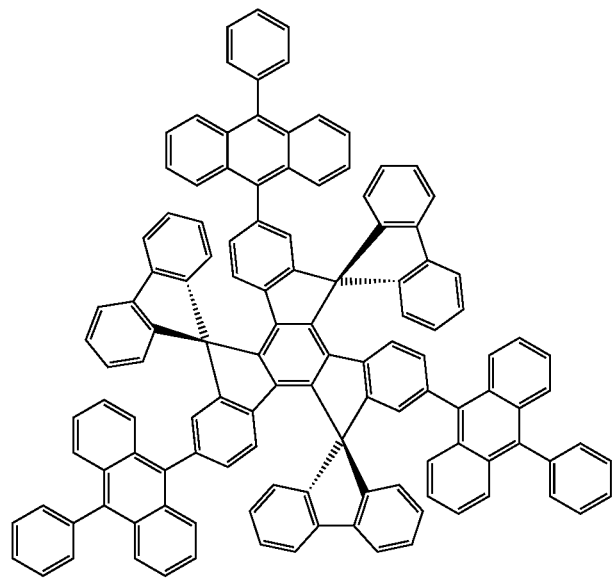

-continued
(12)
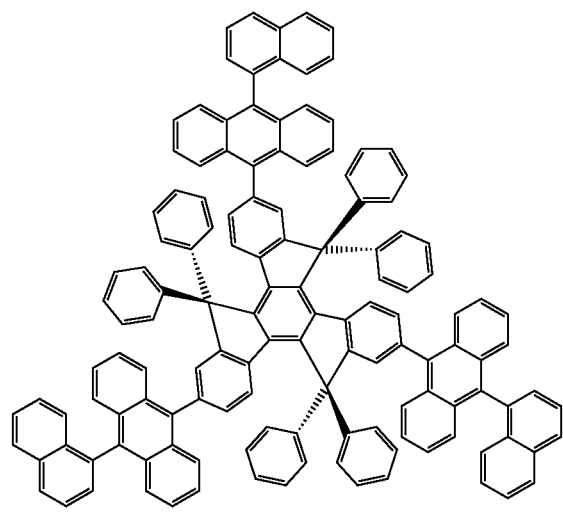
(11)
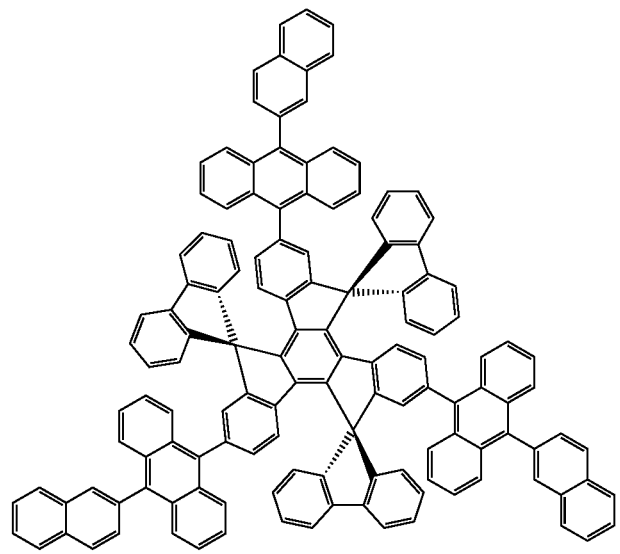

-continued
(13)
(14)
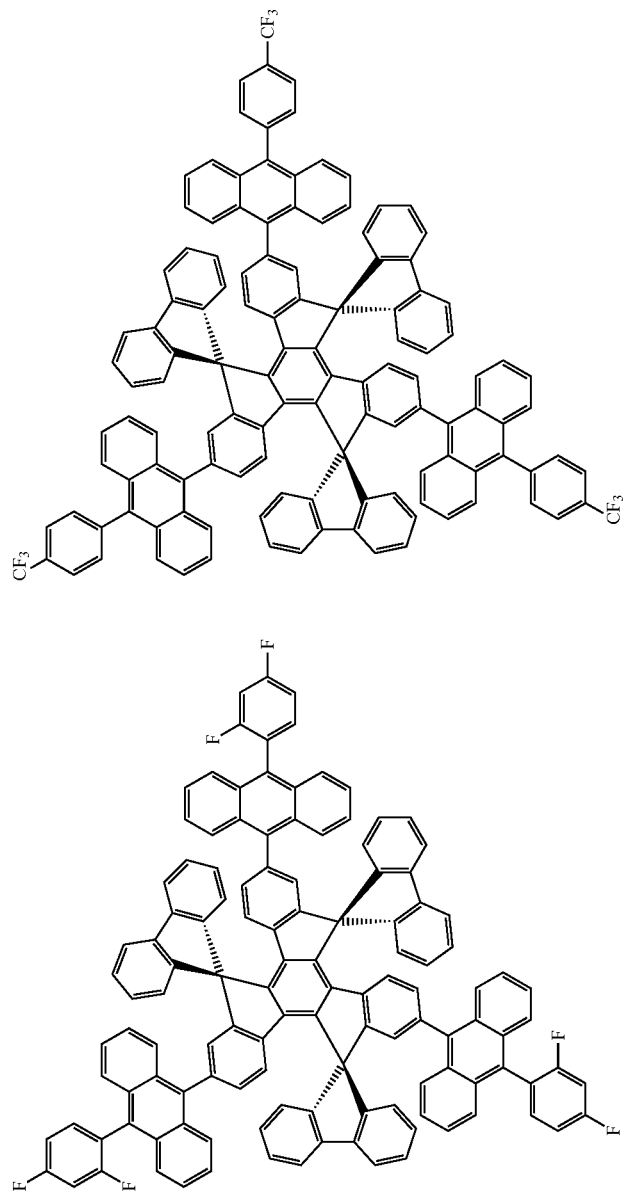

-continued
(16)
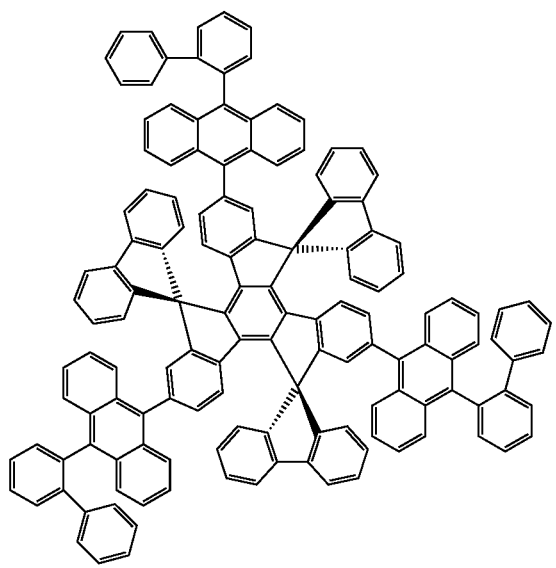
(15)
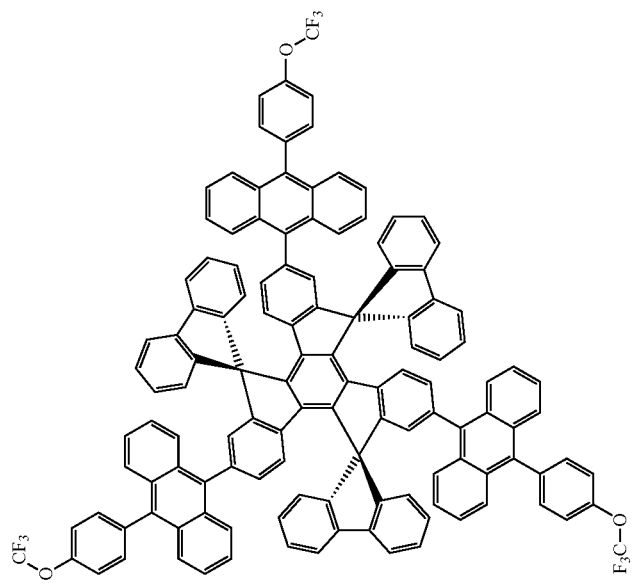

(17)
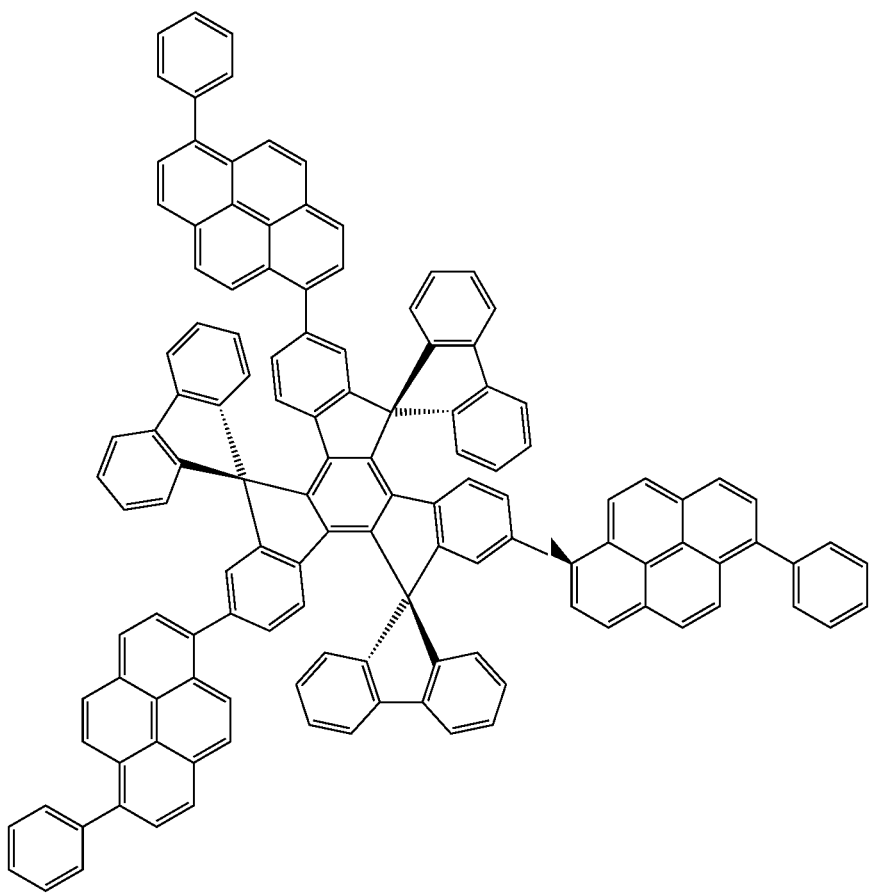

(18)
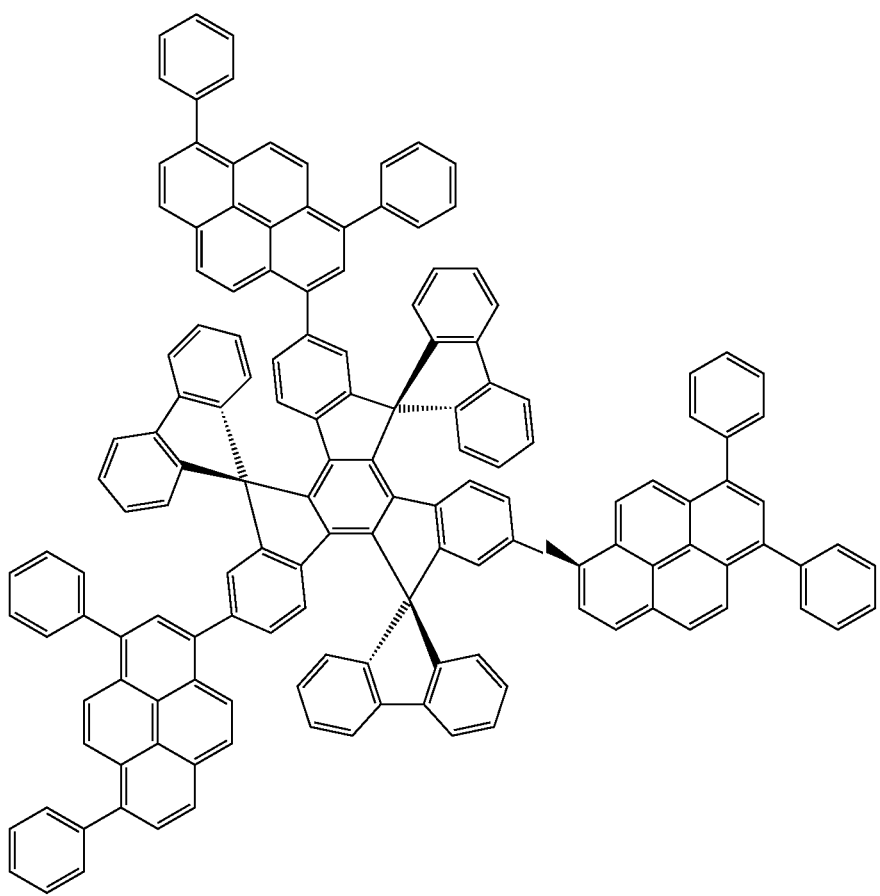

-continued
(19)
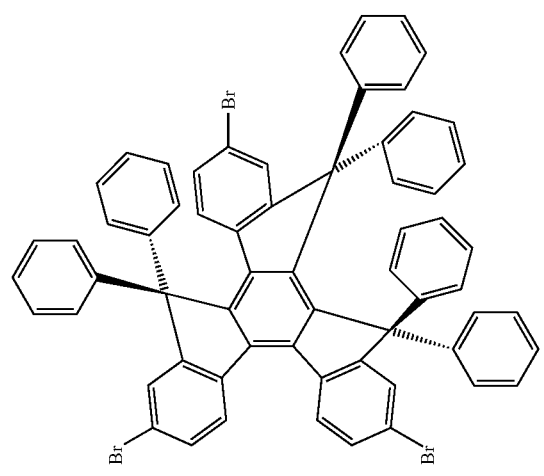
(20)
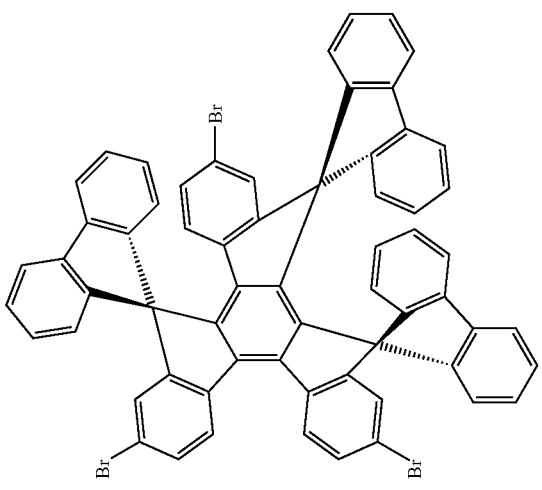
(21)
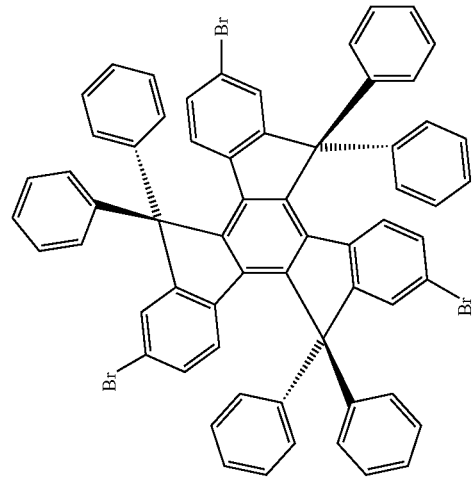
(22)
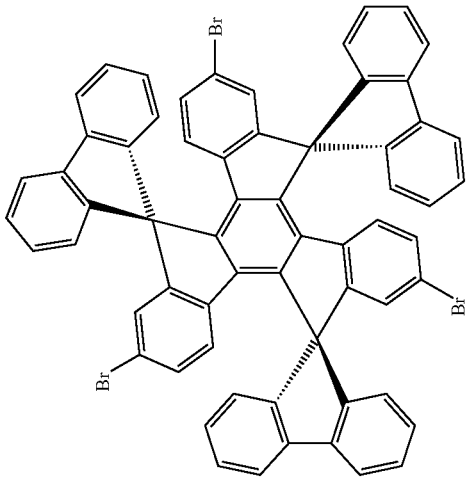

-continued
(24)
(23)
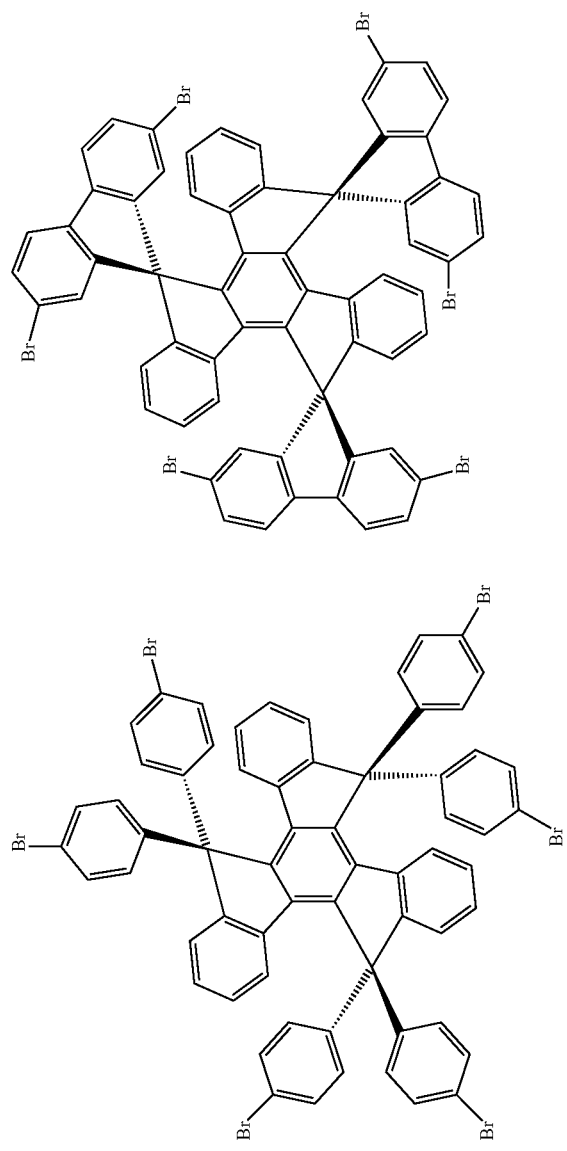

-continued
(26)
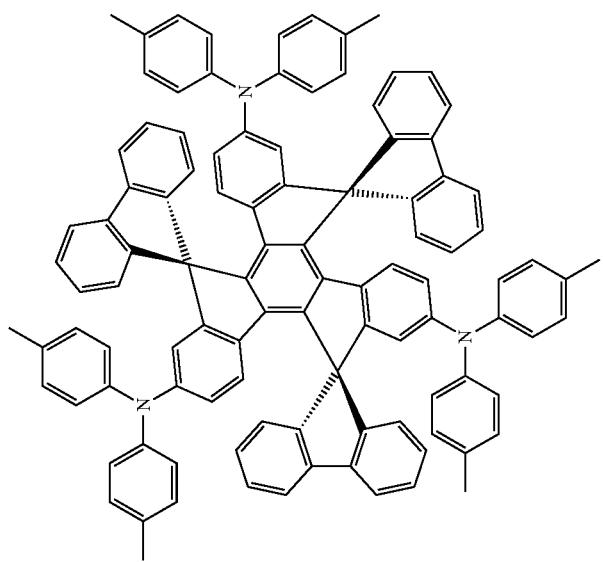
(25)
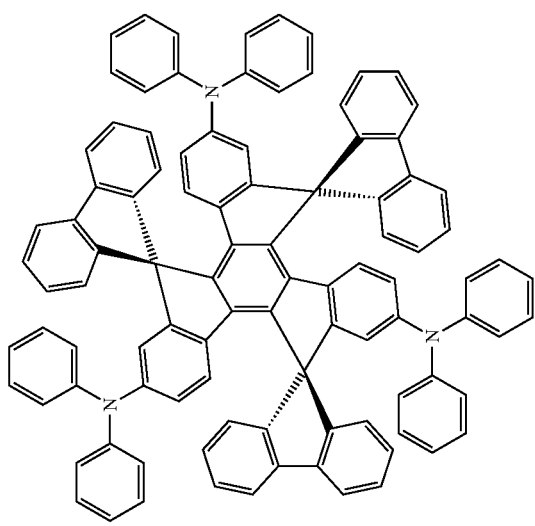

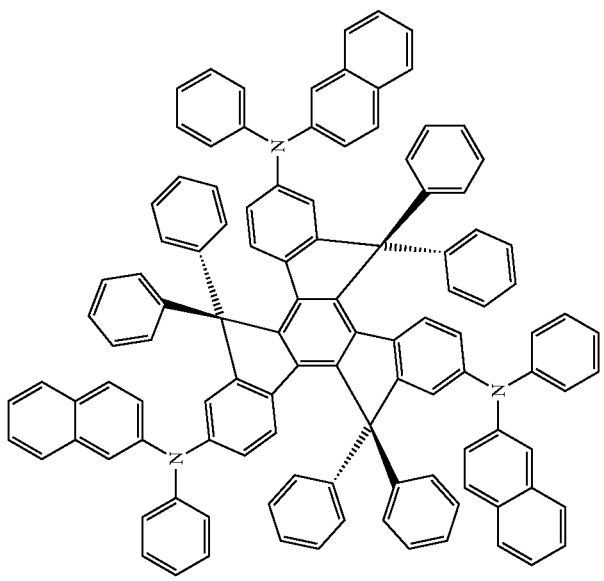
(28)
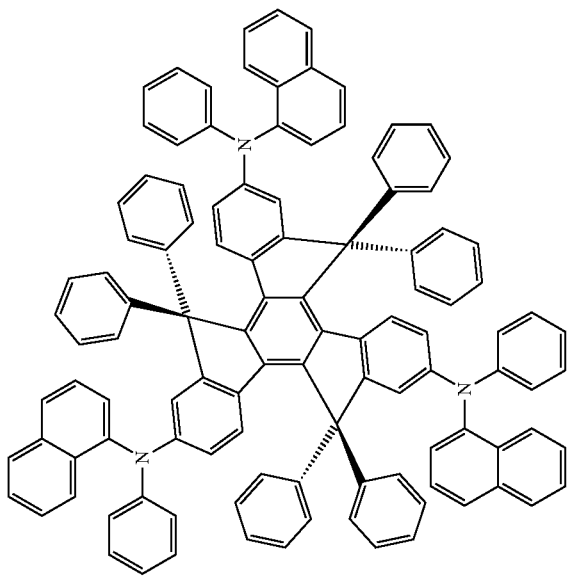
(27)

(29)
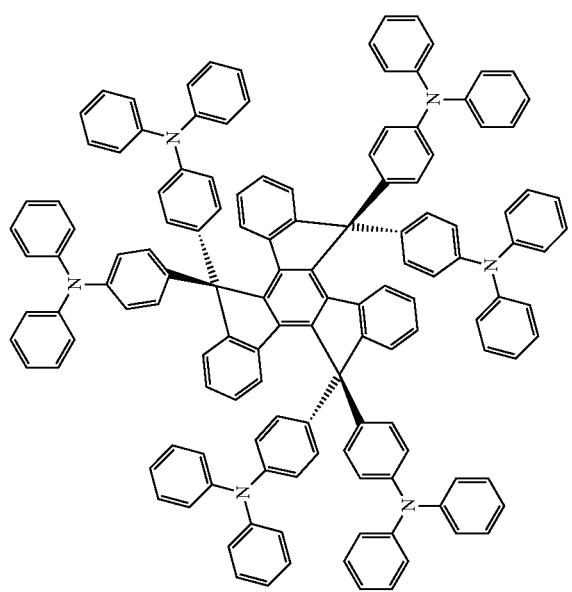

(30)
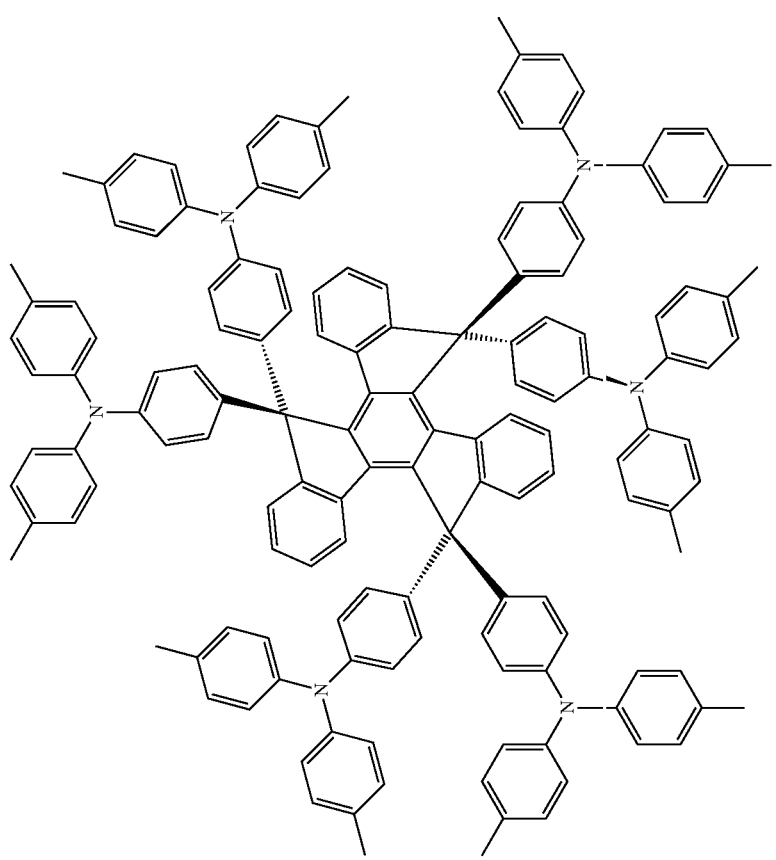

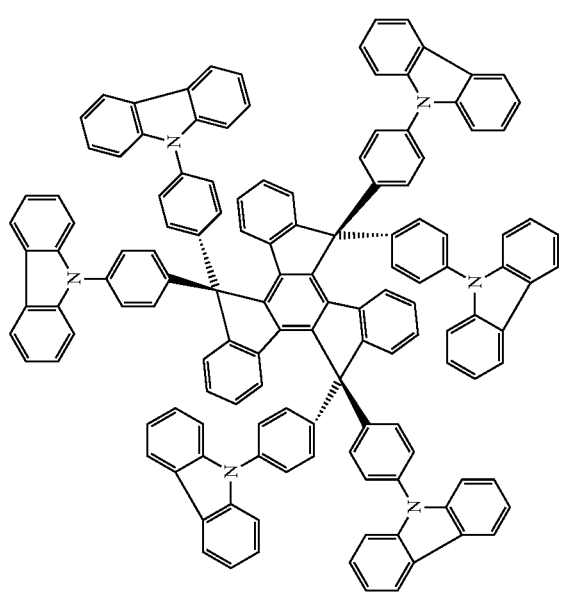
(32)
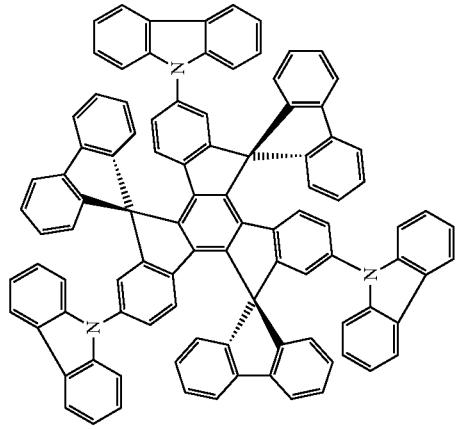
(31)
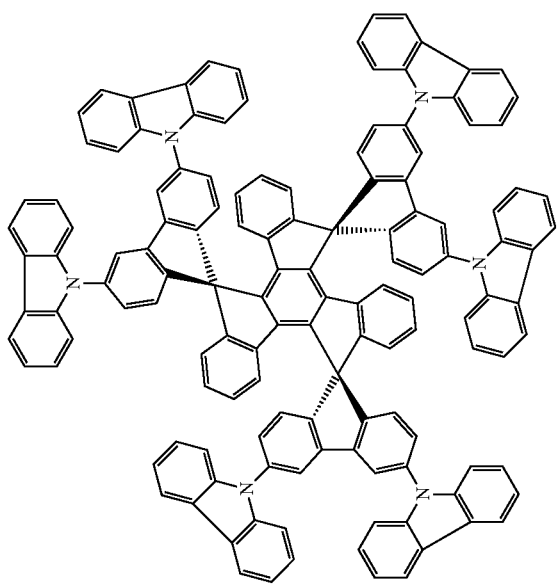
(33)

(34)
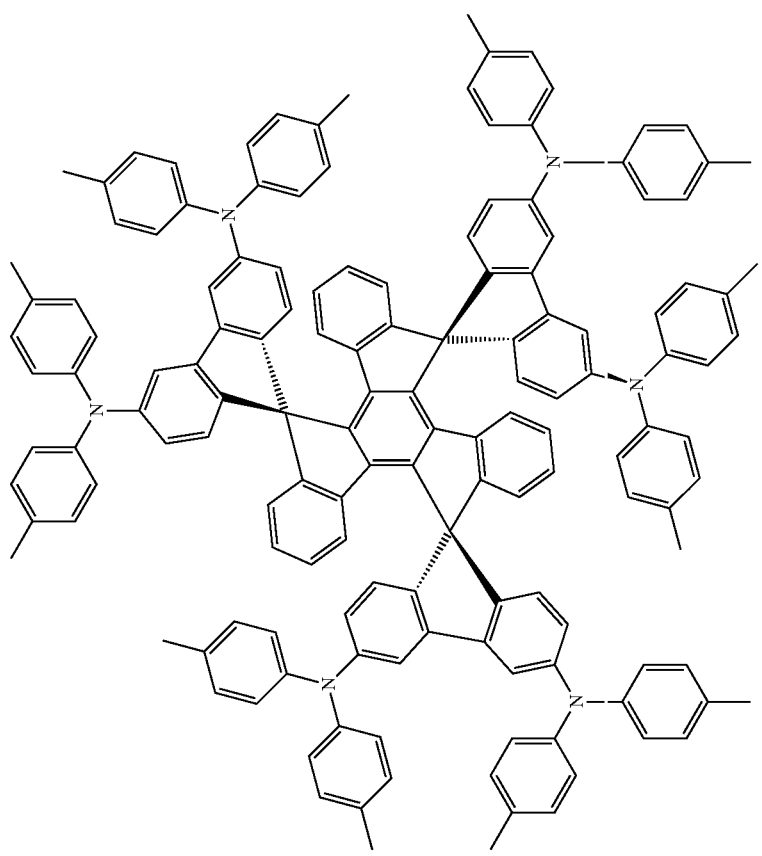

(35)
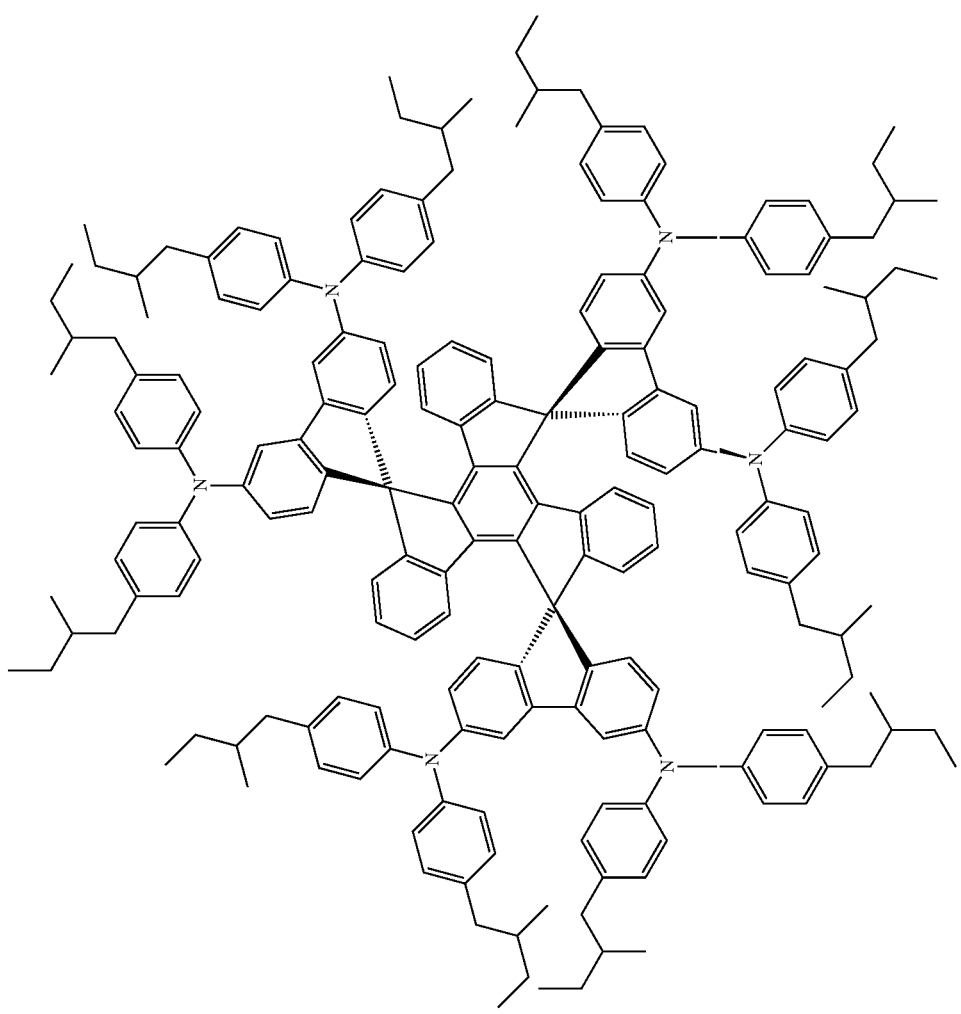

(36)
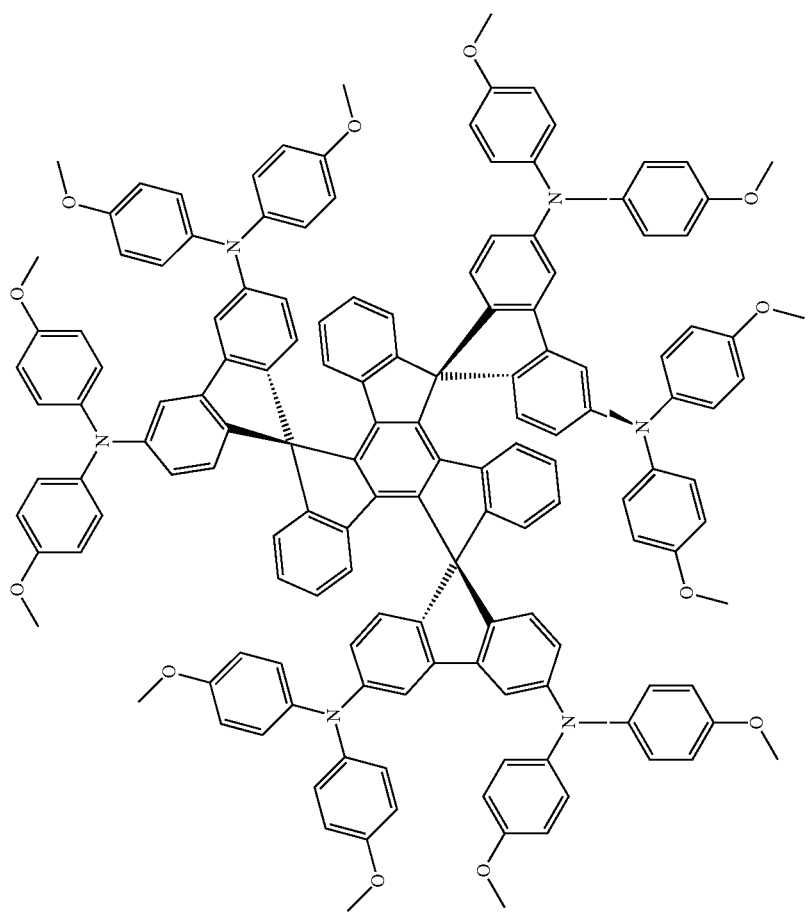

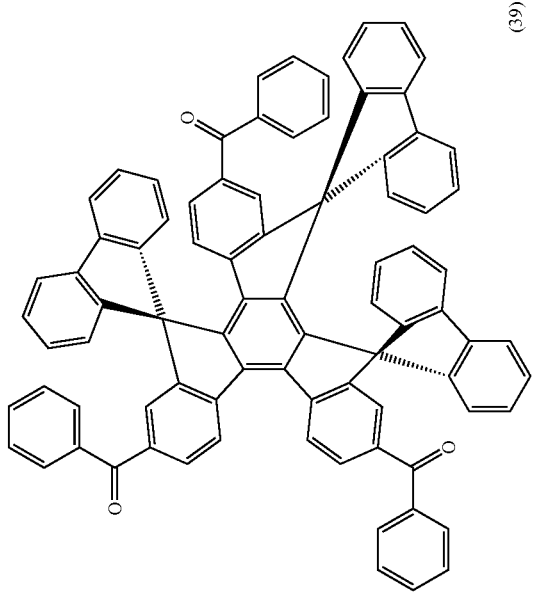
(38)
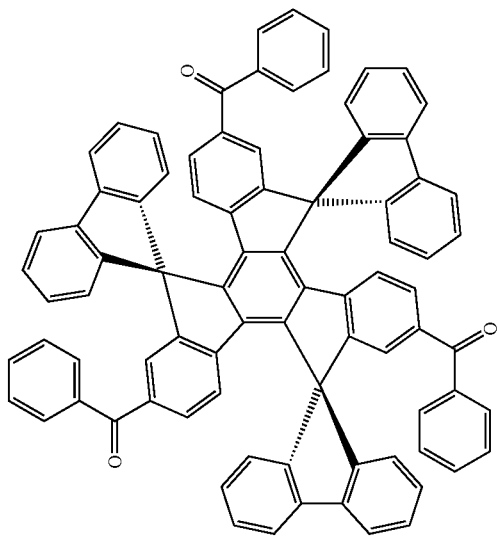
(37)
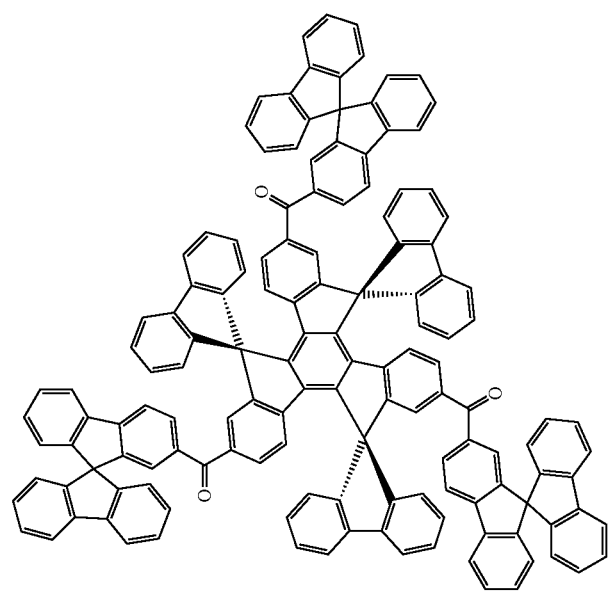
(39)

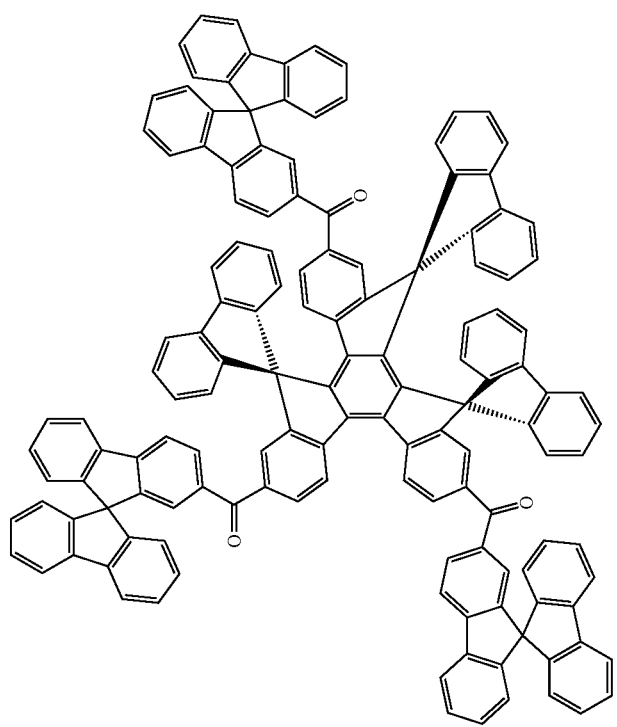
(40)

-continued
(41)
(42)
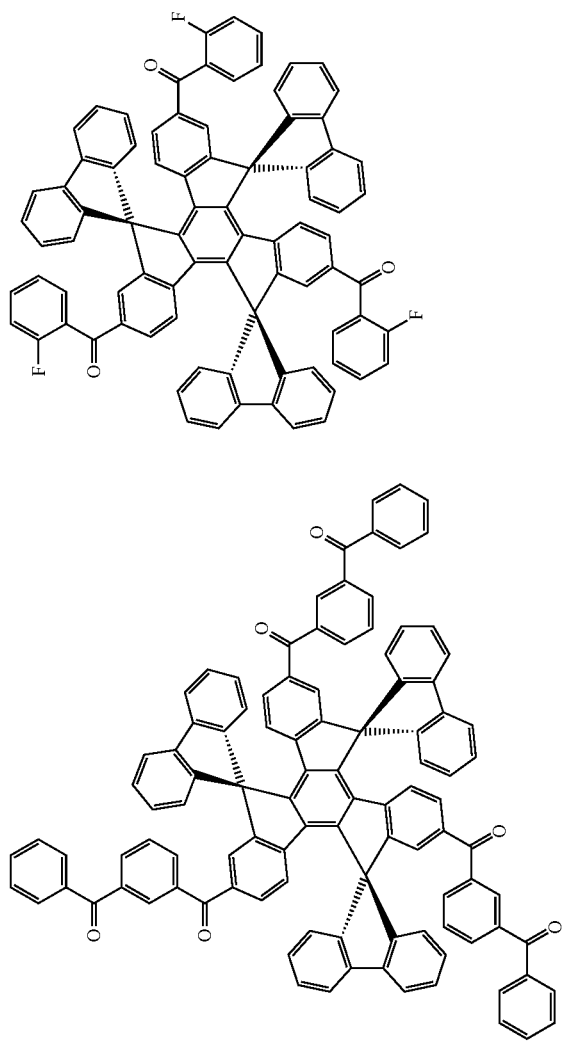

-continued
(44)
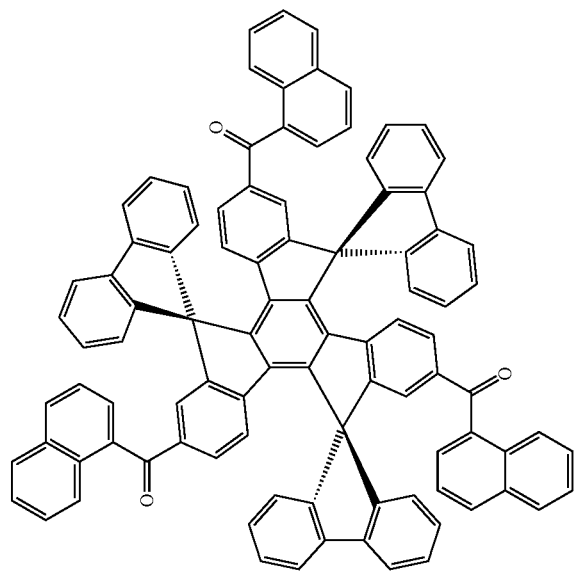
(43)
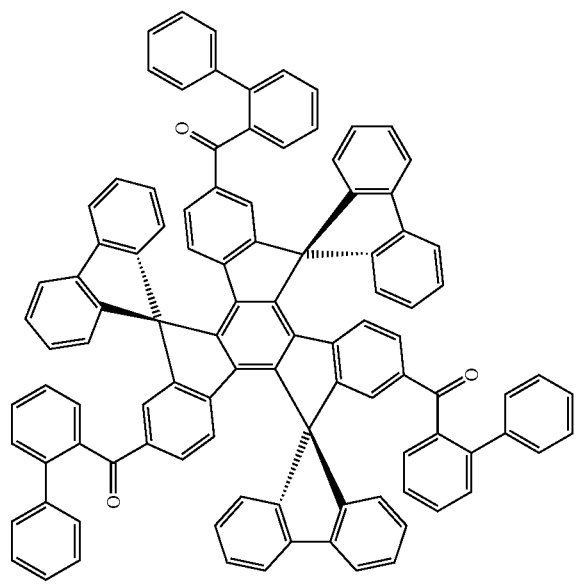

-continued
(46)
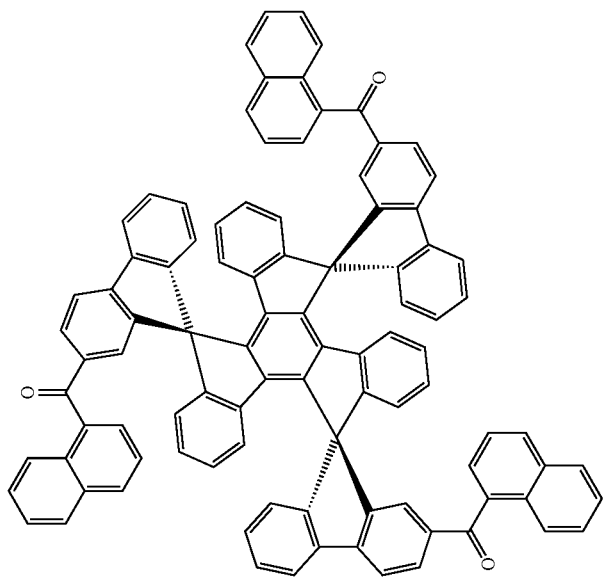
(45)
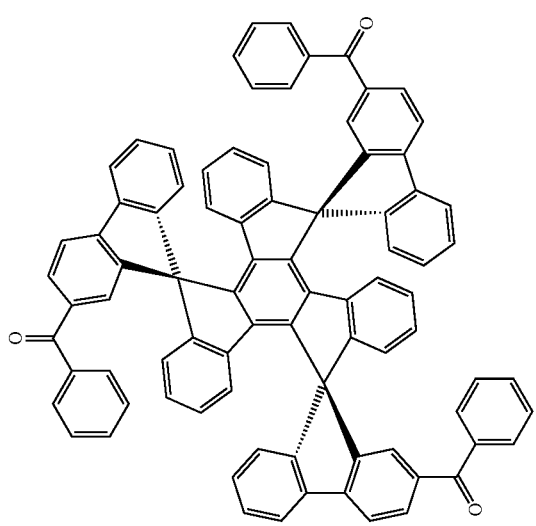

-continued
(48)
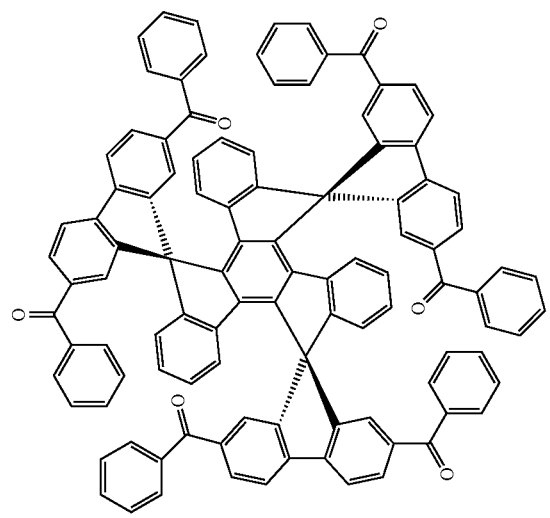
(47)
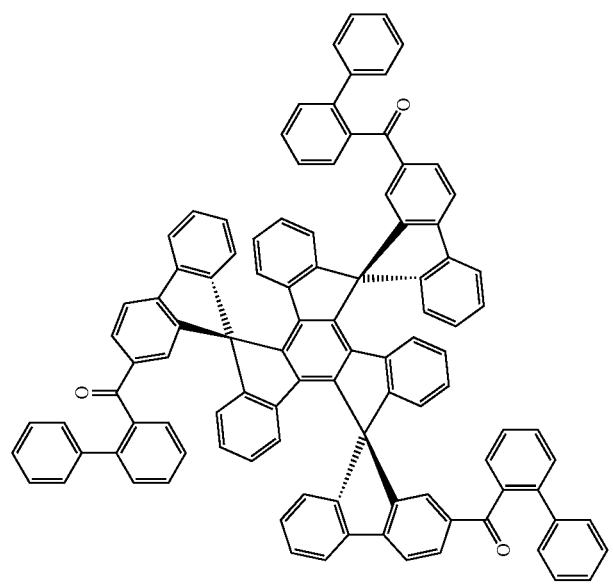

(50)
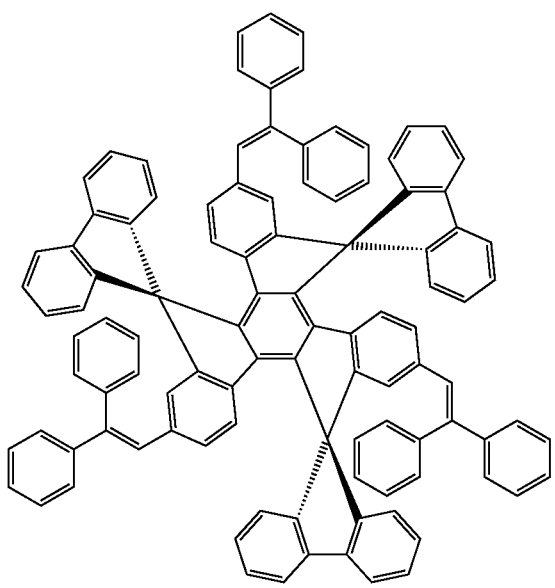
(49)
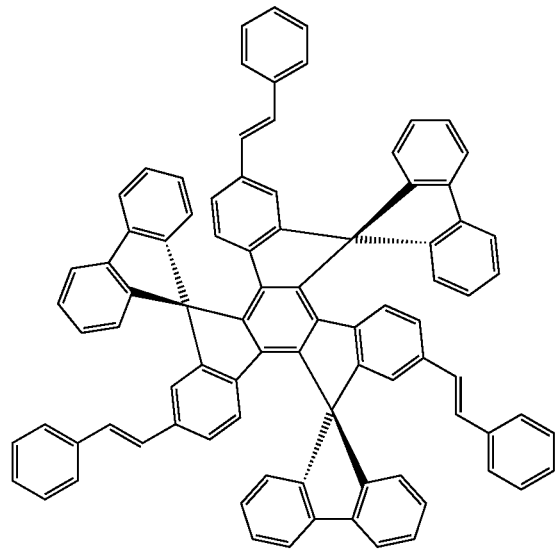

(51)
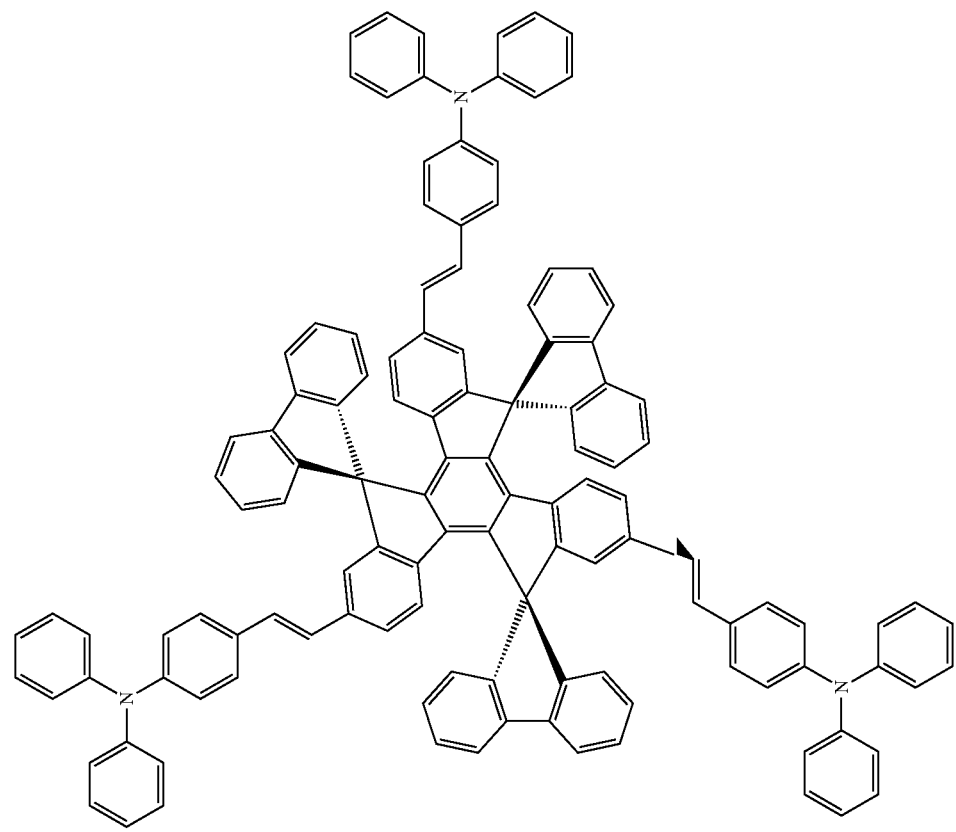

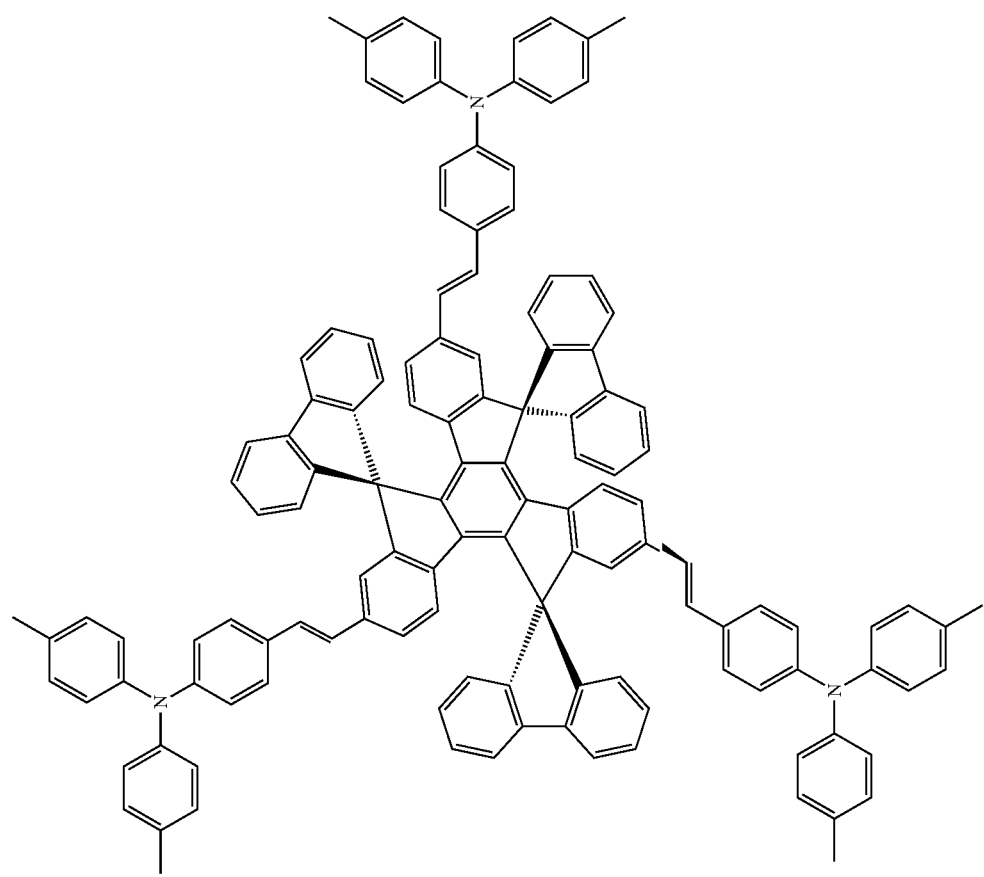
(52)

(53)
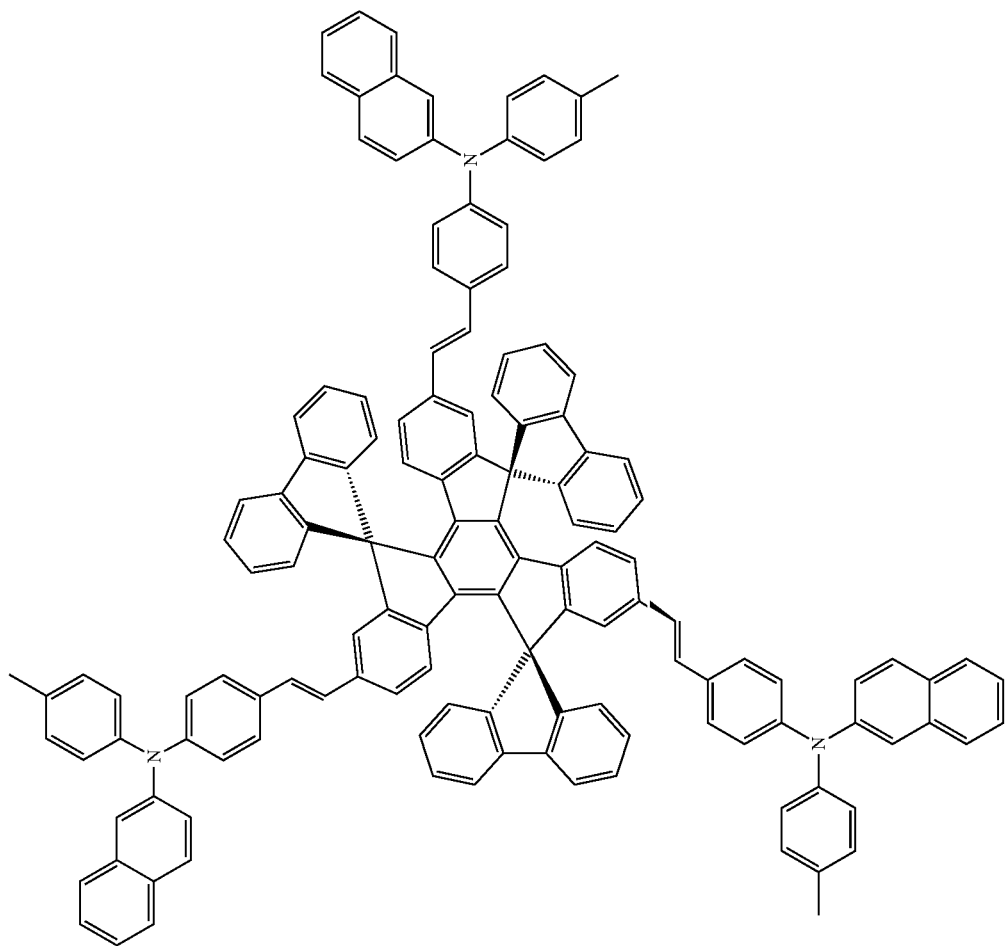

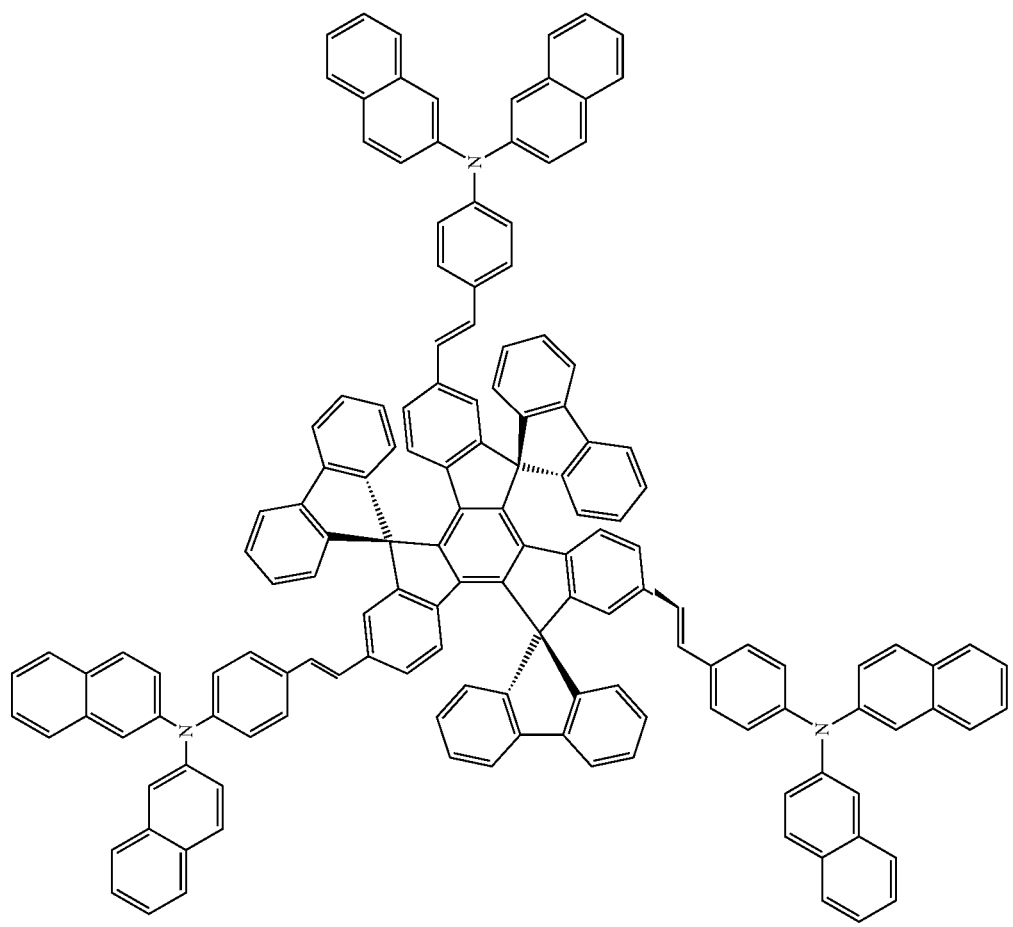

(55)
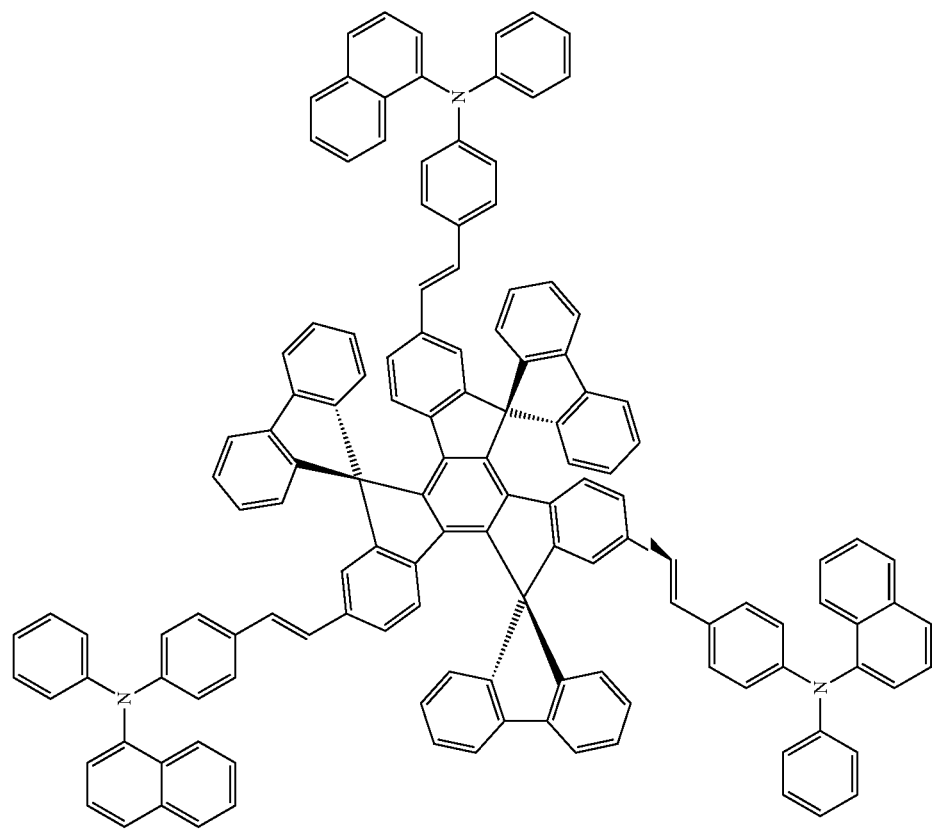

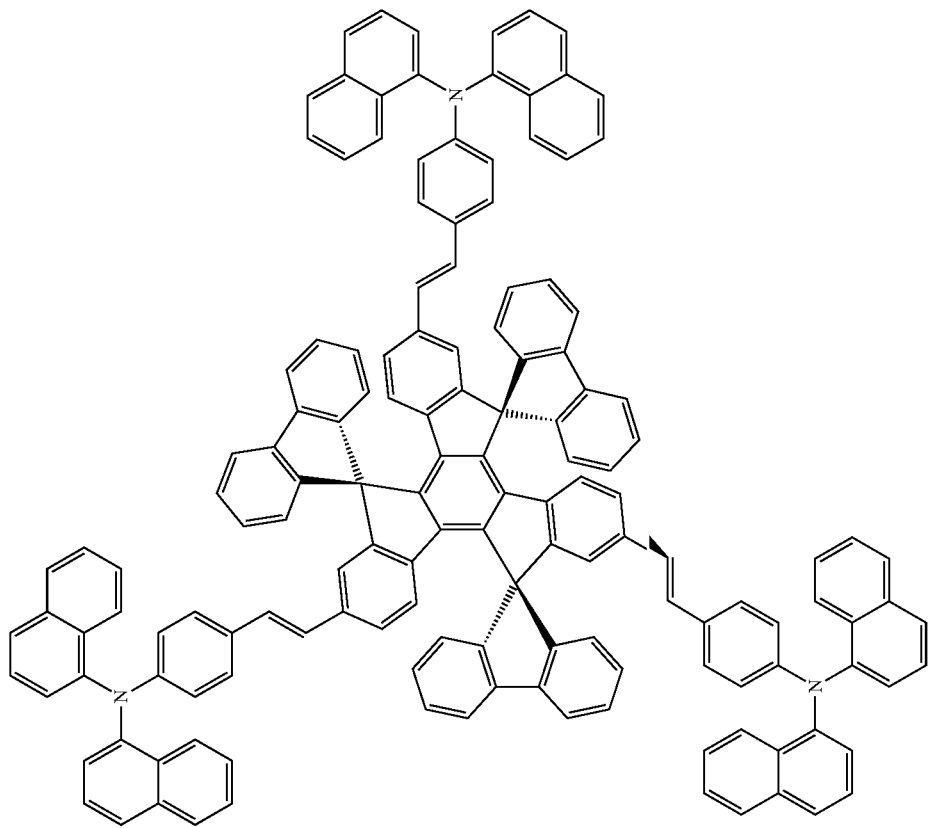

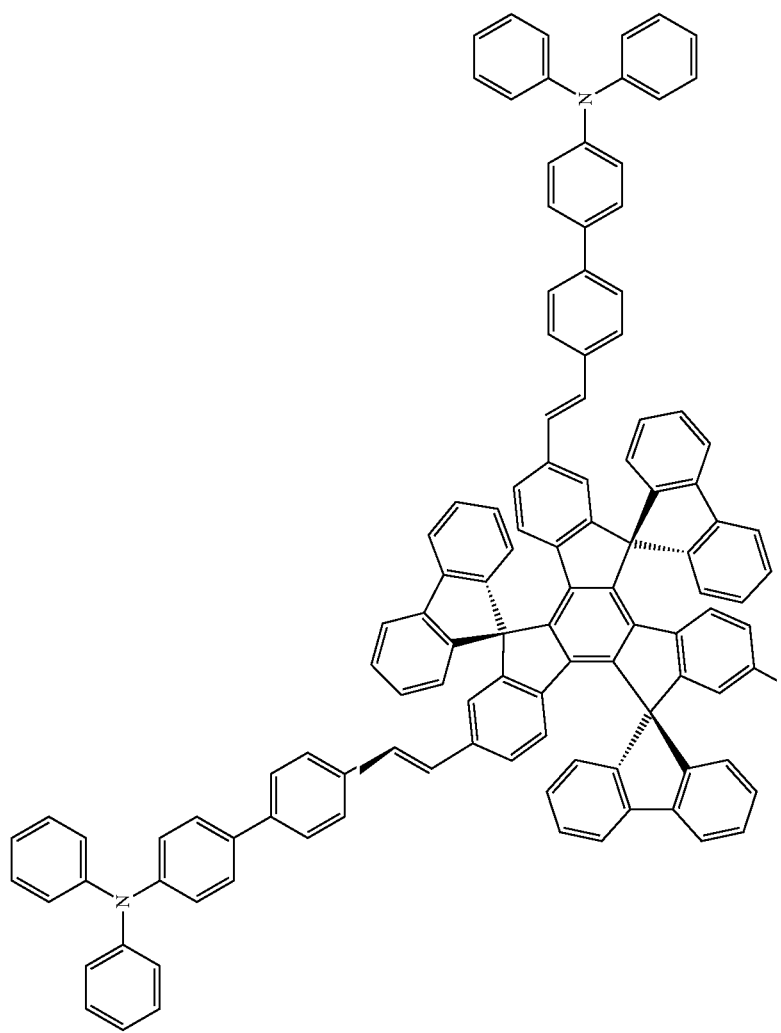

(58)
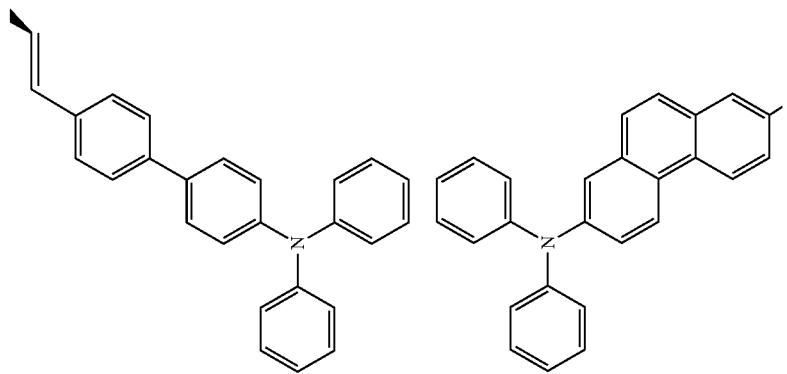

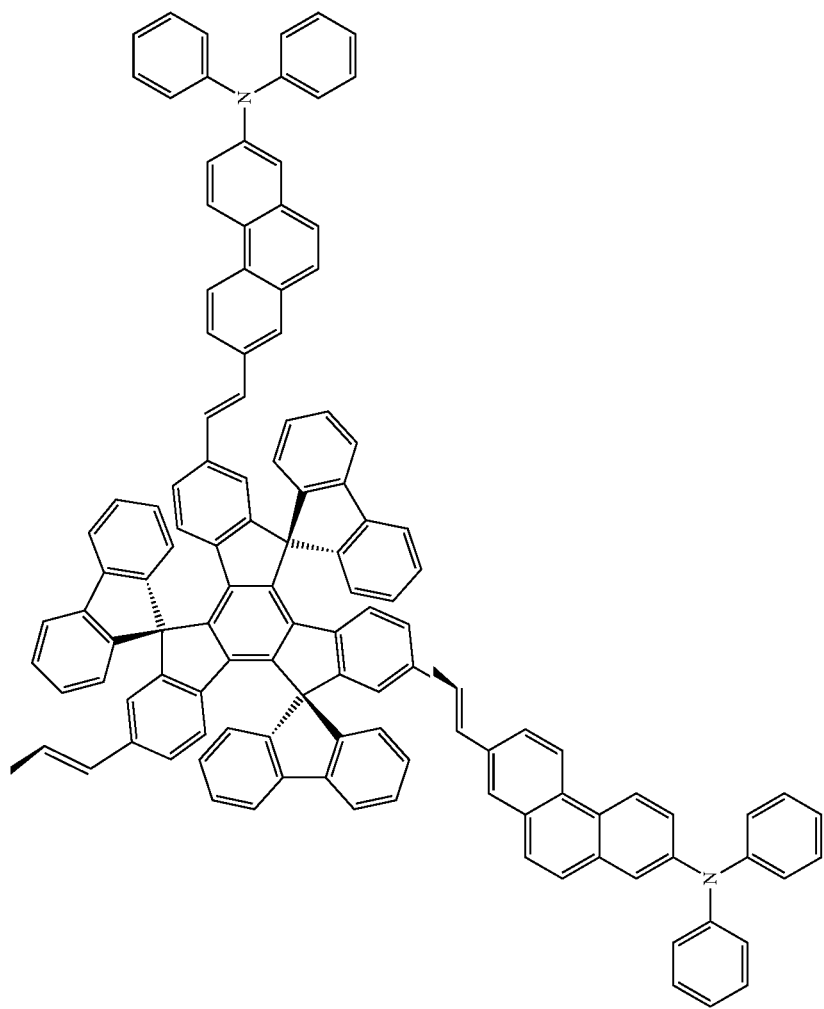

(59)
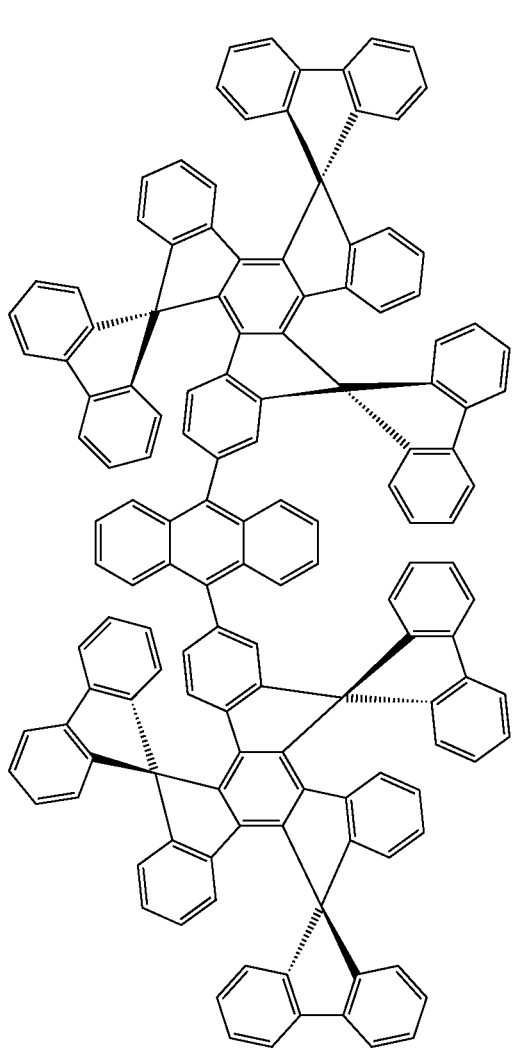
(60)
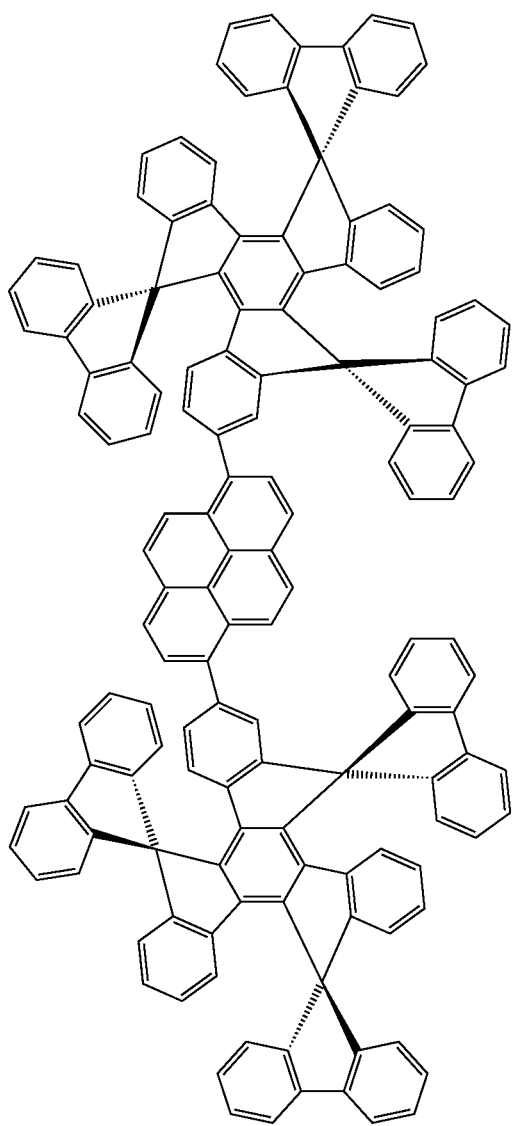

-continued
(62)
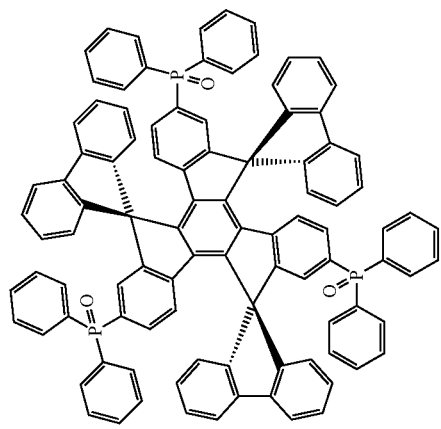
(61)
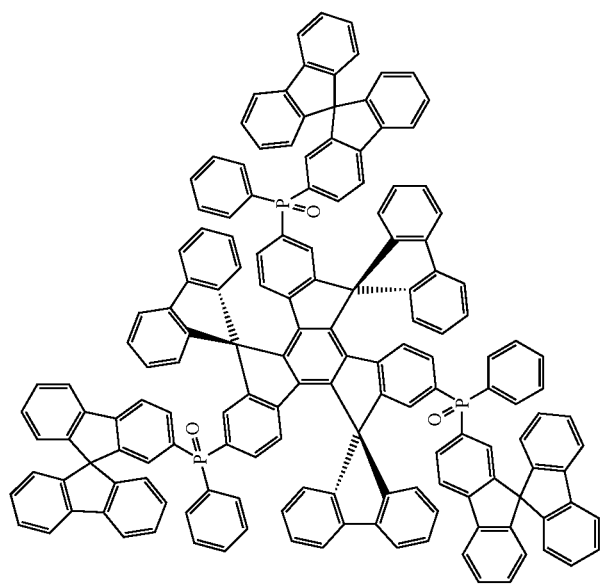

-continued
(64)
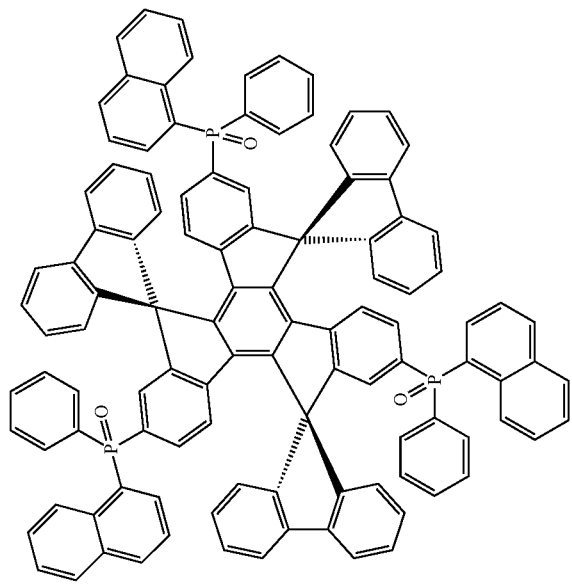
(63)
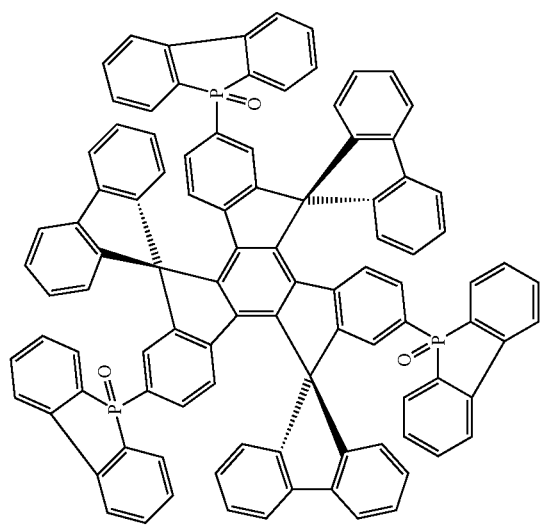

-continued
(66)
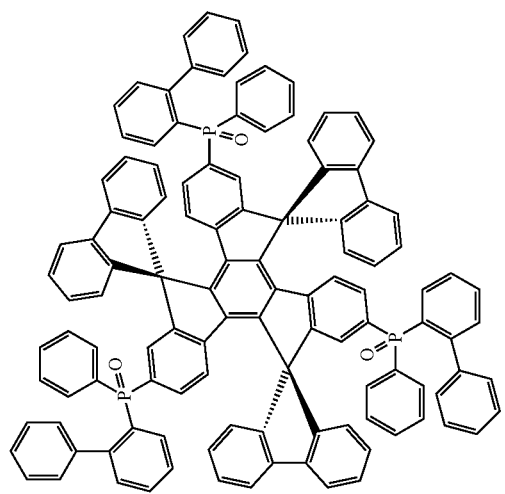
(65)
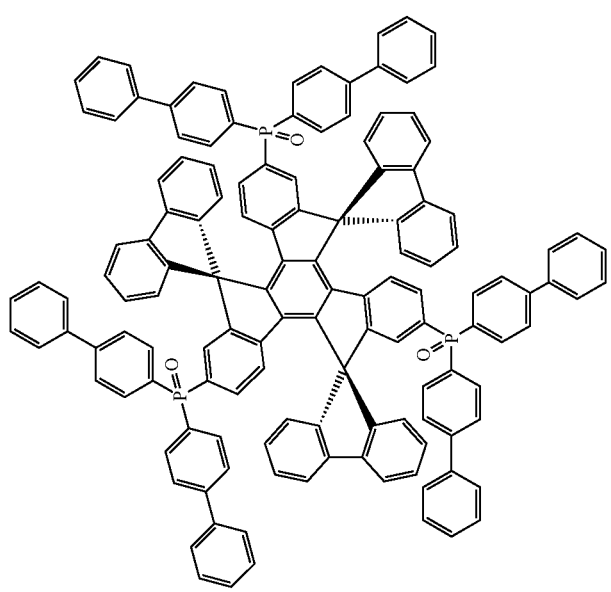

-continued
(68)
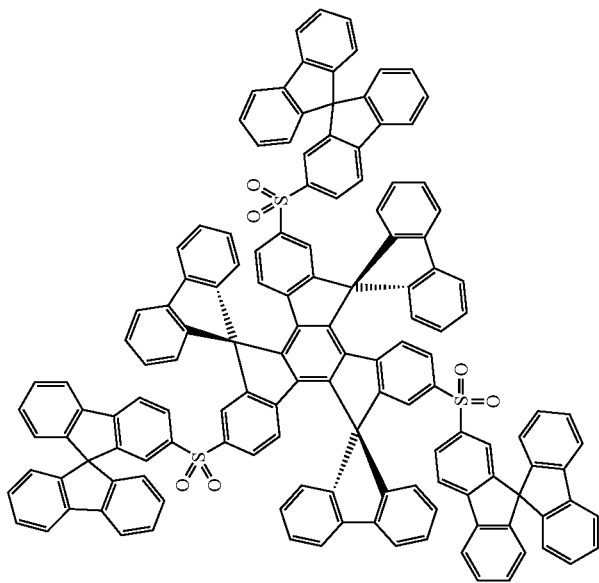
(67)
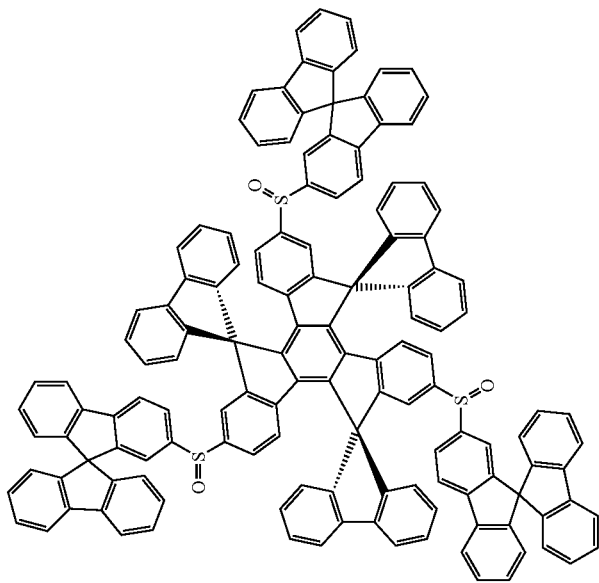

-continued
(70)
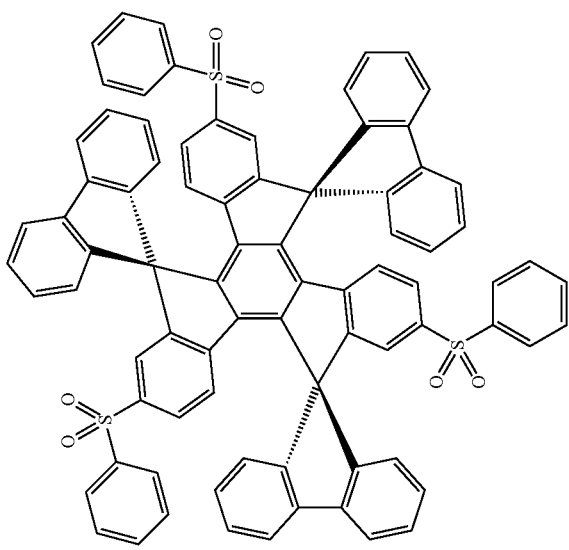
(69)
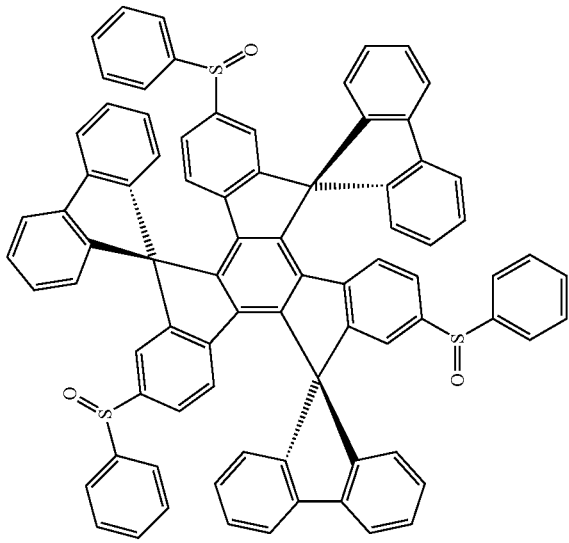

Compounds of the formula (1) or Spiro compounds thereof of the formula (3) can easily be synthesised from commercially available truxene or truxenone. The corresponding isotruxene and spiroisotruxene derivatives of the formulae (2) and (4) can be prepared correspondingly from isotruxene or isotruxenone. Thus, the alkylation of truxene or isotruxene in the 5-, 10- and 15-position or the introduction of aryl substituents in these positions is possible analogously to the reaction of simple fluorenes. Spirotruxene can furthermore be synthesised from truxenone by reaction with an optionally substituted 2-lithiobiphenyl derivative or a corresponding Grignard compound with subsequent acidic ring closure. The functionalisation of the compounds is possible, for example, by Friedel-Crafts alkylation. Functionalisation of the truxene skeleton is furthermore possible by halogenation in the 2-, 7- and/or 12-position, for example by bromination using NBS or elemental bromine. The halogenated compound offers a variety of further functionalisation possibilities, for example arylation by reaction with an arylboronic acid derivative by the Suzuki method, amination by reaction with an arylamine by the Hartwig-Buchwald method, etc. Furthermore, the halogen group can be replaced by an aldehyde group, which can be converted into an alkene in a Wittig-Horner reaction. Thus, the synthesis of stilbene-like systems is possible. Direct introduction of an aldehyde group is also possible in a Vielsmeyer reaction. The halogen functionality can furthermore be lithiated or converted into the Grignard compound. From this, phosphine or phosphine oxide derivatives, for example, are accessible by reaction with a correspondingly substituted phosphine chloride. Direct reaction of truxene or spirotruxene with, for example, an acid chloride by the Friedel-Crafts method to give the corresponding ketone is also possible. Numerous further standard reactions for the functionalisation of truxene and isotruxene and the corresponding spiro compounds are available to the person skilled in the art of organic chemistry.

The invention furthermore relates to oligomers, polymers or dendrimers comprising units of the formula (1) or formula (2) or corresponding spiro units of the formula (3) or formula (4) as recurring units. These units can be copolymerised, for example, via halogen functionalities, such as, for example, structures (19)-(24) depicted above.

The polymers can be conjugated, partially conjugated or non-conjugated polymers. The units of the formula (1) to formula (4) can be bonded into the main chain and/or into the side chain of the polymer. Polymers used in organic electronic devices are usually conjugated or partially conjugated polymers. In general, these polymers are synthesised by palladium-catalysed coupling reactions, in particular Suzuki coupling between an aromatic halide and an aromatic boronic acid or an aromatic boronic acid derivative, for example as described in WO 03/048225.

A preferred embodiment of the invention relates to conjugated or partially conjugated polymers which contain the units of the formula (1) to formula (4) in the main chain or side chain, preferably in the main chain of the polymer.

A further preferred embodiment of the invention relates to branched polymers or dendrimers in which at least one unit of the formula (1) to formula (4) represents a branching point. The unit of the formula (1) to formula (4) particularly preferably represents the centre of a dendrimer.

In a preferred embodiment of the invention, the polymer comprises further recurring units and is thus a copolymer. Preferred further recurring units are selected from fluorenes (for example as described in EP 842208 or WO 00/22026), spirobifluorenes (for example as described in EP 707020, EP 894107 or EP 04028865.6), phenylenes (for example as described in WO 92/18552), carbazoles (for example as described in WO 04/070772 and WO 04/113468), thiophenes (for example as described in EP 1028136), dihydrophenanthrenes (for example as described in WO 05/014689), indenofluorenes (for example as described in WO 04/041901 and WO 04/113412), phenanthrenes (for example as described in the unpublished application DE 102004020298.2), aromatic ketones (for example as described in WO 05/040302) or also from a plurality of these units. Phosphorescent metal complexes may also represent recurring units of the polymer (for example as described in WO 02/068435 or as described in the unpublished application DE 102004032527.8). Further preferred recurring units are selected from hole-transport units, electron-transport units and emitting units, as known to the person skilled in the art in the area of light-emitting polymers.

The invention furthermore relates to the use of compounds of the formulae (1) and (2) and the corresponding spiro compounds of the formula (3) and formula (4) and corresponding oligomers, polymers and dendrimers according to the invention in organic electronic devices.

The invention furthermore relates to organic electronic devices, in particular organic electroluminescent devices, comprising at least one organic layer which comprises at least one compound of the formula (1) and/or formula (2) or a spiro compound of the formula (3) and/or formula (4) or an oligomer, polymer or dendrimer according to the invention which comprises at least one recurring unit of the formula (1) to formula (4).

For use of the compounds of the formula (1) to formula (4), the substitution patterns described above are particularly preferred.

The organic electronic device is preferably selected from the group consisting of organic and polymeric light-emitting diodes (OLEDs, PLEDs), organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (O-LECs) and organic laser diodes (O-lasers). Particular preference is given to organic and polymeric light-emitting diodes.

The organic electronic device usually comprises an anode, a cathode and at least one organic layer which comprises at least one compound of the formula (1) or formula (2). In organic electroluminescent devices, at least one of the organic layers is an emission layer. The emission here can be fluorescence or phosphorescence, or a plurality of different emitters may also be present in one layer or in a plurality of layers, where some of the emitters exhibit fluorescence and some of the emitters exhibit phosphorescence. It may also be preferred for the organic electronic device to comprise further layers in addition to the anode, cathode and emission layer. These can be, for example: hole-injection layer, hole-transport layer, hole-blocking layer, electron-transport layer and/or electron-injection layer. However, it should be pointed out at this point that each of these layers does not necessarily have to be present.

In a preferred embodiment of the invention, the compound of the formula (1) or formula (2) is employed in an emission layer. It can be employed here as the pure substance, but is preferably employed as host material in combination with a fluorescent or phosphorescent dopant. Which substituents on the compounds according to the invention are particularly preferred for these functions has already been described in detail at the outset. In principle, all fluorescent or phosphorescent dopants, as described in the literature and described below in greater detail, are suitable for this purpose.

In fluorescent devices, the dopant is preferably selected from the class of the monostyrylamines, distyrylamines, tristyrylamines, tetrastyrylamines and arylamines. A monostyrylamine is taken to mean a compound which contains a styryl group and at least one amine, which is preferably aromatic. A distyrylamine is taken to mean a compound which contains two styryl groups and at least one amine, which is preferably aromatic. A tristyrylamine is taken to mean a compound which contains three styryl groups and at least one amine, which is preferably aromatic. A tetrastyrylamine is taken to mean a compound which contains four styryl groups and at least one amine, which is preferably aromatic. For the purposes of this invention, an arylamine or an aromatic amine is taken to mean a compound which contains three aromatic or heteroaromatic ring systems bonded directly to the nitrogen. The styryl groups are particularly preferably stilbenes, which may also be further substituted on the double bond or on the aromatic ring. Examples of dopants of this type are substituted and unsubstituted tristilbenamines or further dopants which are described, for example, in the unpublished patent applications DE 102004031000.9, EP 04028407.7 and EP 05001891.0.

The proportion of the compound of the formula (1) or formula (2) here as host in the fluorescent mixture of the emission layer is usually between 1 and 99.9% by weight, preferably between 50 and 99.5% by weight, particularly preferably between 80 and 99% by weight, in particular between 90 and 99% by weight. Correspondingly, the proportion of the fluorescent dopant is between 0.1 and 99% by weight, preferably between 0.5 and 50% by weight, particularly preferably between 1 and 20% by weight, in particular between 1 and 10% by weight.

In phosphorescent devices, the dopant is preferably selected from the class of the metal complexes containing at least one element having an atomic number of greater than 20, preferably greater than 38 and less than 84, particularly preferably greater than 56 and less than 80. The phosphorescent emitters used are preferably metal complexes containing molybdenum, tungsten, rhenium, ruthenium, osmium, rhodium, iridium, palladium, platinum, silver, gold or europium, in particular iridium or platinum.

The ligands on the metal are preferably monoanionic, bidentate-chelating ligands. Suitable for this purpose are, in particular, ligands which form a metal-carbon bond and furthermore a coordinative bond from a donor atom, in particular nitrogen, oxygen or phosphorus, to the metal. The metal complex preferably contains at least one ligand of this type, particularly preferably at least two ligands of this type. The formation of a metal-carbon and metal-nitrogen bond is preferred here. Both coordinating groups may be cyclic, for example phenylpyridine or derivatives thereof, or they may also be acyclic, for example ligands which bond via pyridine and a vinyl C atom. Further ligands may also be present, for example β-diketonates, etc. In a particularly preferred embodiment of the invention, the complex contains only bidentate-chelating ligands which form a metal-carbon bond.

Preferred phosphorescent OLEDs comprise, as phosphorescent emitter, at least one compound of the formulae (A) to (D)

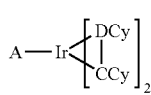

Formula (A)

Formula (B)

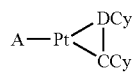

Formula (C)

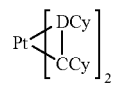

Formula (D)

where the following applies to the symbols and indices used:

DCy is on each occurrence, identically or differently, a cyclic group which contains at least one donor atom, preferably nitrogen or phosphorus, via which the cyclic group is bonded to the metal and which may itself carry one or more substituents R; the groups DCy and CCy are connected to one another via at least one covalent bond;

CCy is on each occurrence, identically or differently, a cyclic group which contains a carbon atom via which the cyclic group is bonded to the metal and which may itself carry one or more substituents R;

A is on each occurrence, identically or differently, a monoanionic, bidentate-chelating ligand, preferably a diketonate ligand;

R has the same meaning as indicated above.

The cyclic groups CCy and DCy may be monocyclic or polycyclic and are preferably aromatic or heteroaromatic. A plurality of the ligands may furthermore also be linked via one or more substituents R as bridging unit to form a larger polypodal ligand, and/or a bridge between CCy and DCy may be present in addition to the direct covalent bond.

Particular preference is given to structures of the formulae (B) and (D) in which no further ligand A is present.

Examples of phosphorescent emitters are revealed in the applications WO 00/70655, WO 01/41512, WO 02/02714, WO 02/15645, EP 1191613, EP 1191612, EP 1191614, WO 04/081017 and the unpublished applications DE 10345572.8, EP 04029182.5 and EP 05002237.5.

The proportion of the compound of the formula (1) or formula (2) as host in the phosphorescent mixture is usually between 1 and 99.9% by weight, preferably between 50 and 99.5% by weight, particularly preferably between 70 and 99% by weight, in particular between 80 and 95% by weight. Correspondingly, the proportion of the phosphorescent dopant is between 0.1 and 99% by weight, preferably between 0.5 and 50% by weight, particularly preferably between 1 and 30% by weight, in particular between 5 and 20% by weight.

Preference is furthermore given to organic electroluminescent devices, characterised in that a plurality of emitting compounds are used in the same layer or a plurality of emitting layers are present, where at least one of the emitting layers comprises at least one compound of the formula (1) or formula (2). This device particularly preferably has a plurality of emission maxima between 380 nm and 750 nm, resulting overall in white emission. The emitting compounds employed here can be both those which exhibit fluorescence and also those which exhibit phosphorescence.

In a further preferred embodiment of the invention, the compound of the formula (1) or formula (2) is employed as electron-transport material as the pure substance or in a mixture, preferably as the pure substance, in an electron-transport layer in an organic electronic device, in particular in a fluorescent or phosphorescent organic electroluminescent device.

In a further preferred embodiment of the invention, the compound of the formula (1) or formula (2) is employed as hole-blocking material as the pure substance or in a mixture, preferably as the pure substance, in a hole-blocking layer, in particular in a phosphorescent organic electroluminescent device.

In a further preferred embodiment of the invention, the compound of the formula (1) or formula (2) is employed as hole-transport material as the pure substance or in a mixture, preferably as the pure substance, in a hole-transport layer or in a hole-injection layer in an organic electronic device, in particular in a fluorescent or phosphorescent organic electroluminescent device. This is the case, in particular, if the compound of the formula (1) or formula (2) contains one or more diarylamine groups, carbazole groups or triarylamine groups.

In a further preferred embodiment of the invention, the compound of the formula (1) or formula (2) is employed as fluorescent dopant, preferably in combination with a host material, in an emission layer in a fluorescent organic electroluminescent device.

This is the case, in particular, if the compound of the formula (1) or formula (2) contains one or more vinylaryl groups, in particular one or more stilbene groups, optionally in combination with one or more arylamine groups. Suitable host materials are then the compounds usually used as host materials, preferably selected from the classes of the oligoarylenes (for example 2,2',7,7'-tetraphenylspirobifluorene as described in EP 676461 or dinaphthylanthracene), in particular the oligoarylenes containing condensed aromatic groups, the oligoarylenevinylenes (for example DPVBi or spiro-DPVBi as described in EP 676461), the polypodal metal complexes (for example as described in WO 04/081017), the hole-conducting compounds (for example as described in WO 04/058911) and the electron-conducting compounds, in particular ketones, phosphine oxides, sulfoxides, etc. (for example as described in the unpublished application DE 102004008304.5), but also the above-described host materials according to the invention. Particularly preferred host materials are selected from the classes of the oligoarylenes containing naphthalene, anthracene and/or pyrene, the oligoarylenevinylenes, the ketones, the phosphine oxides and the sulfoxides. Very particularly preferred host materials are selected from the classes of the oligoarylenes containing anthracene and/or pyrene, the phosphine oxides and the sulfoxides. The proportion of the compound of the formula (1) or formula (2) as dopant in the mixture is preferably as already described above for dopants in fluorescent organic electroluminescent devices.

It may furthermore be preferred for compounds of the formula (1) or formula (2) to be used simultaneously in a plurality of layers and/or functions. Thus, they can be employed simultaneously, for example, both in one or more emission layers and also in one or more electron-transport layers and/or hole-blocking layers and/or hole-transport layers. The compounds of the formula (1) or formula (2) in the different layers may be identical or different.

Preference is furthermore given to an organic electronic device, characterised in that one or more layers are coated by a sublimation process, in which the materials are vapour-deposited in vacuum sublimation units at a pressure below $10^{-5}$ mbar, preferably below $10^{-6}$ mbar, particularly preferably below $10^{-7}$ mbar.

Preference is likewise given to an organic electronic device, characterised in that one or more layers are coated by the OVPD (organic vapour phase deposition) process or with the aid of carrier-gas sublimation, in which the materials are generally applied at a pressure between $10^{-5}$ mbar and 1 bar.

Preference is furthermore given to an organic electronic device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing.

The devices described above have the following surprising advantages over the prior art:
1. The stability of corresponding devices is greater compared with systems in accordance with the prior art, which is evident, in particular, from a longer lifetime of the OLED.
2. The materials have a high glass-transition temperature, which makes them highly suitable for use in organic electronic devices.
3. The compounds according to the invention are readily soluble, which represents a prerequisite for purification and especially for application from solution.
4. The compounds according to the invention have high symmetry. Without wishing to be tied to a particular theory, we assume that high symmetry is necessary for good electronic properties.

The present application text and also the examples below are directed to the use of compounds of the formula (1) or formula (2) in relation to OLEDs and the corresponding displays. In spite of this restriction of the description, it is possible for the person skilled in the art, without further inventive step, also to use corresponding compounds for further uses in other organic electronic devices, in particular those as described above.

The invention is explained by the following examples without wishing it to be restricted thereby.

EXAMPLES

The starting materials for the following syntheses were purchased from Aldrich (4-tert-butylbenzoyl chloride) or from Lancaster (truxenone, 2-bromobiphenyl) or from Fluka ($AlCl_3$). The IR spectra were measured using a Perkin-Elmer 298 and Shimadzu 470, the NMR spectra using a Bruker AC 200.

Example 1

Synthesis of Spirotruxene

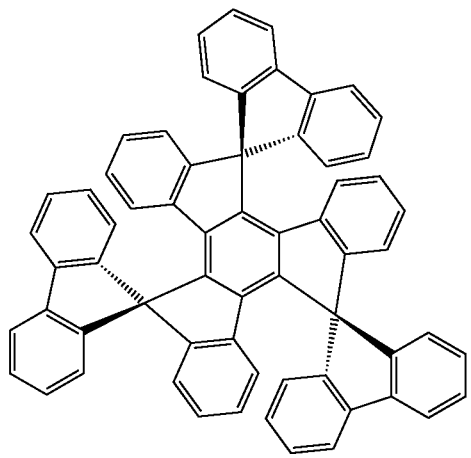

13 ml (32.5 mmol) of n-butyllithium (2.5M in hexane) are added over the course of 30 minutes at −78° C. to a solution of 0.9 g (14.3 mmol, 2.4 ml) of 2-bromobiphenyl, dissolved in 20 ml of anhydrous THF, and the mixture is then brought to 0° C. The lithiated compound is transferred into a dropping funnel using a syringe and slowly added dropwise at 0° C. to a suspension of 0.5 g (1.3 mmol) of truxenone in 30 ml of anhydrous THF. The solution is brought to room temperature and held at this temperature for 4 h, then saturated ammonium chloride solution is added. The aqueous phase is extracted with $CH_2Cl_2$ (3×15 ml), and the organic phase is dried over anhydrous sodium sulfate. Removal of the solvent gives a reddish liquid, which is a mixture of a plurality of isomers. The liquid is dissolved in 10 ml of glacial acetic acid and heated under reflux, a few drops of concentrated HCl are then added, and the mixture is heated under reflux for a further minute. Water is added until turbidity forms, and the mixture is then cooled to room temperature and filtered. The acidic aqueous phase is extracted with $CH_2Cl_2$ and dried over anhydrous sodium sulfate, and the solvent is then removed in a rotary evaporator, giving a beige solid (850 mg, 78%), which is insoluble in most conventional organic solvents. The NMR spectrum of the compound in DMSO shows that it is spirotruxene.

$^1$H-NMR (DMSO, 200 MHz), δ [ppm]=7.62-7.27 (36H, m, ArH).

$^{13}$C-NMR (DMSO, 50 MHz), δ [ppm]=141.4, 141.2, 140.2, 139.5 (all quaternary C atoms); 129.6, 129.1, 128.8, 128.0, 127.9, 126.7, 126.6, 125.6 (all CH).

Example 2

Synthesis of 2,7,12-tetrakis(para-tert-butylbenzoyl)spirotruxene

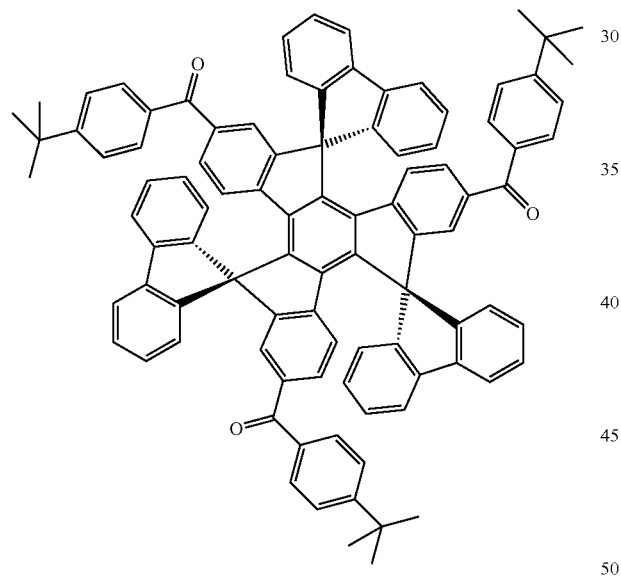

240 mg (1.8 mmol) of finely powdered, anhydrous $AlCl_3$ are added at 0° C. with stirring to 500 mg (0.6 mmol) of spirotruxene, dissolved in 30 ml of $CH_2Cl_2$. 354 mg (1.8 mmol, 0.35 ml) of 4-tert-butylbenzoyl chloride in 10 ml of $CH_2Cl_2$ are then added dropwise with stirring over the course of 10 minutes. The reaction mixture is refluxed for 4 h. The solvent is removed under reduced pressure, and 50 g of ice and 25 ml of 2M HCl solution are added to the residue. The aqueous phase is extracted with $CH_2Cl_2$ (3×15 ml). The organic phase is washed with saturated $NaHCO_3$ solution (20 ml) and water (20 ml), dried and concentrated. The product is purified by column chromatography (silica, hexane: $CH_2Cl_2$ 1:1), giving 54 mg of the product.

Melting point: 153-154° C.

$^1$H-NMR (CDCl$_3$, 200 MHz), δ [ppm]=8.03-7.49 (45H, m, ArH), 1.34 (27H, —C(CH$_3$)$_3$)

$^{13}$C-NMR (CDCl$_3$, 50 MHz), δ [ppm]=172.6 (C=O), 157.5 (ArC-tBu), 150.2, 148.3, 148.0, 147.5, 141.7, 140.8, 138.2, 135.1, 130.3-120.4, 66.8 (spiro-C), 35.1, 31.1.

IR (solid, cm$^{-1}$): 1680 (C=O).

The invention claimed is:

1. A compound of Formula (1) and Formula (2)

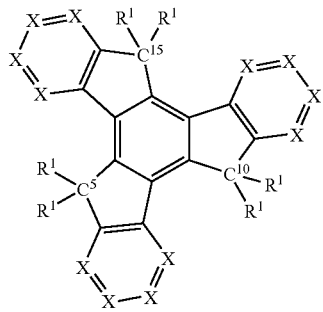

Formula (1)

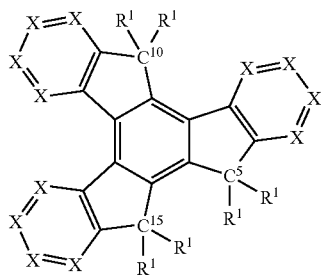

Formula (2)

wherein

X is CR;

R is on each occurrence, identically or differently, H, F, Cl, Br, I, CN, NH$_2$, NO$_2$, OH, N(R$^2$)$_2$, Si(R$^2$)$_3$, B(OR$^2$)$_2$, B(OH)$_2$, Sn(R$^2$)$_3$, C(=O)R$^2$, P(R$^2$)$_2$, P(=O)(R$^2$)$_2$, S(=O)R$^2$, S(=O)$_2$R$^2$, a straight-chain alkyl, alkoxy or thioalkoxy group having up to 40 C atoms, optionally substituted by R$^3$, or a branched or cyclic alkyl, alkoxy or thio-alkoxy group having 3 to 40 C atoms, optionally substituted by R$^3$, wherein one or more non-adjacent C atoms of said straight-chain, branched or cyclic alkyl, alkoxy, or thio-alkoxy group are optionally replaced by N—R$^3$, O, S, O—CO—O, CO—NR$^3$, —CR$^3$=CR$^3$—, or —C≡C—, and wherein one or more H atoms are optionally replaced by F, Cl, Br, I, CN, or an aromatic or heteroaromatic ring system, optionally substituted by one or more non-aromatic radicals R, or a combination of two, three or four of these systems; and wherein two or more substituents R optionally define a monocyclic or polycyclic aliphatic, monocyclic or polycyclic aromatic, or monocyclic or polycyclic heteroaromatic ring system with one another;

R$^1$ is one each occurrence, identically or differently, H, F, Cl, Br, I, CN, a straight-chain alkoxy or thioalkoxy chain having up to 40 C atoms, optionally substituted by R$^3$, or a branched or cyclic alkyl, alkoxy or thioalkoxy chain having 3 to 4 C atoms, optionally substituted by R$^3$, wherein one or more non-adjacent C atoms of said straight-chain, branched or cyclic alkyl, alkoxy, or thio-alkoxy group are optionally replaced by N—$R^3$, O, S, O—CO—O, CO—O, CO—$NR^3$, —$CR^3$=$CR^3$—, or —C≡C—, and wherein one or more H atoms are optionally replaced by F, Cl, Br, I, CN, or an aromatic or heteroaromatic ring system, optionally substituted by one or more radicals R, or a combination of two, three or four of these systems; and wherein two or more substituents $R^1$ optionally define a monocyclic or polycyclic aliphatic, monocyclic or polycyclic aromatic, or monocyclic or polycyclic heteroaromatic ring system with one another; with the proviso that the two substituents $R^1$ bonded to $C^5$ and/or the two substituents $R^1$ bonded to $C^{10}$ and/or the two substituents $R^1$ bonded to $C^{15}$ are an aromatic or heteroaromatic ring system;

$R^2$ is on each occurrence, identically or differently, a straight-chain alkyl group having up to 40 C atoms, optionally substituted by $R^3$, or a branched or cyclic alkyl chain having 3 to 40 C atoms, optionally substituted by $R^3$, wherein one or more non-adjacent C atoms of said straight-chain, branched or cyclic alkyl, alkoxy, or thio-alkoxy group are optionally replaced by N—$R^3$, O, S, O—CO—O, CO—O, CO—$NR^3$, —$CR^3$=$CR^3$—, or —C≡C—, and wherein one or more H atoms are optionally replaced by F, Cl, Br, I, CN, or an aromatic or hetero-aromatic ring system, optionally substituted by one or more non-aromatic radicals R, or a combination of two, three or four of these systems; and wherein two or more substituents $R^2$ optionally define a monocyclic or polycyclic aliphatic, monocyclic or polycyclic aromatic, or monocyclic or polycyclic heteroaromatic ring system with one another;

$R^3$ is on each occurrence, identically or differently, H or an aliphatic or aromatic hydrocarbon radical having up to 20 C atoms.

2. The compound of claim 1 having structures according to Formula (3) or Formula (4)

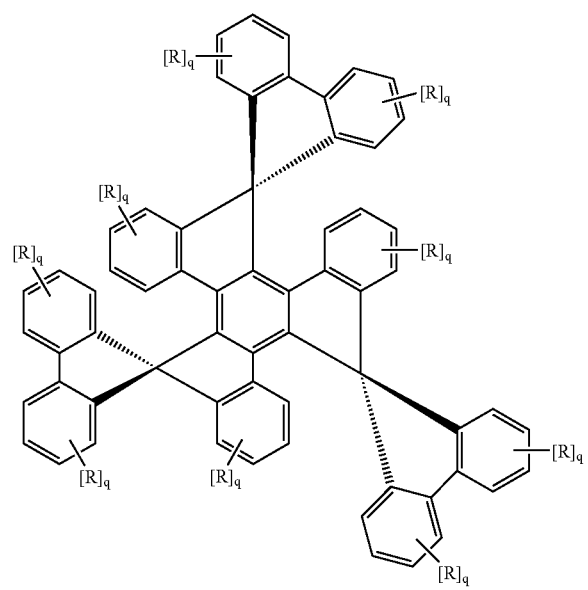

Formula (3)

-continued

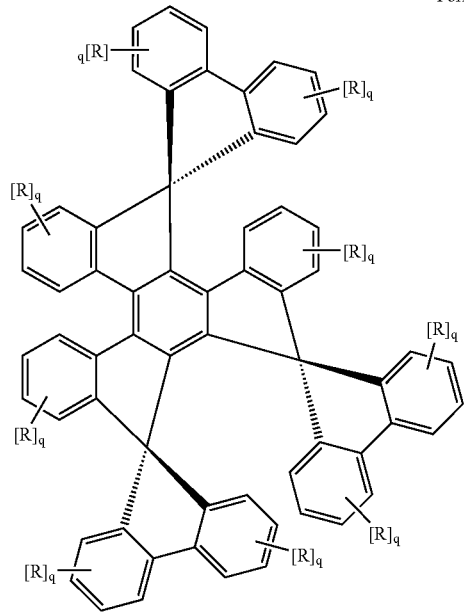

Formula (4)

wherein

R is on each occurrence, identically or differently, H, F, Cl, Br, I, CN, $NH_2$, $NO_2$, OH, $N(R^2)_2$, $Si(R^2)_3$, $B(OR^2)_2$, $B(OH)_2$, $Sn(R^2)_3$, C(=O)$R^2$, $P(R^2)_2$, P(=O)$(R^2)_2$, S(=O)$R^2$, S(=O)$_2R^2$, a straight-chain alkyl, alkoxy or thioalkoxy group having up to 40 C atoms, optionally substituted by $R^3$, or a branched or cyclic alkyl, alkoxy or thio-alkoxy group having 3 to 40 C atoms, optionally substituted by $R^3$, wherein one or more non-adjacent C atoms of said straight-chain, branched or cyclic alkyl, alkoxy, or thio-alkoxy group are optionally replaced by N—$R^3$, O, S, O—CO—O, CO—$NR^3$, —$CR^3$=$CR^3$—, or —C≡C—, and wherein one or more H atoms are optionally replaced by F, Cl, Br, I, CN, or an aromatic or heteroaromatic ring system, optionally substituted by one or more non-aromatic radicals R, or a combination of two, three or four of these systems; and wherein two or more substituents R optionally define a monocyclic or polycyclic aliphatic, monocyclic or polycyclic aromatic, or monocyclic or polycyclic heteroaromatic ring system with one another; and q is on each occurrence, identically or differently, 0, 1, 2, 3 or 4.

3. The compound of claim 1, wherein each $R^1$ is an aromatic or heteroaromatic ring system optionally substituted by R or unsubstituted.

4. The compound of claim 3, wherein said aromatic or heteroaromatic ring systems have 5 to 30 aromatic ring atoms.

5. The compound of claim 2 having structures according to Formula (1a) and Formula (2a)

Formula (1a)

Formula (2a)

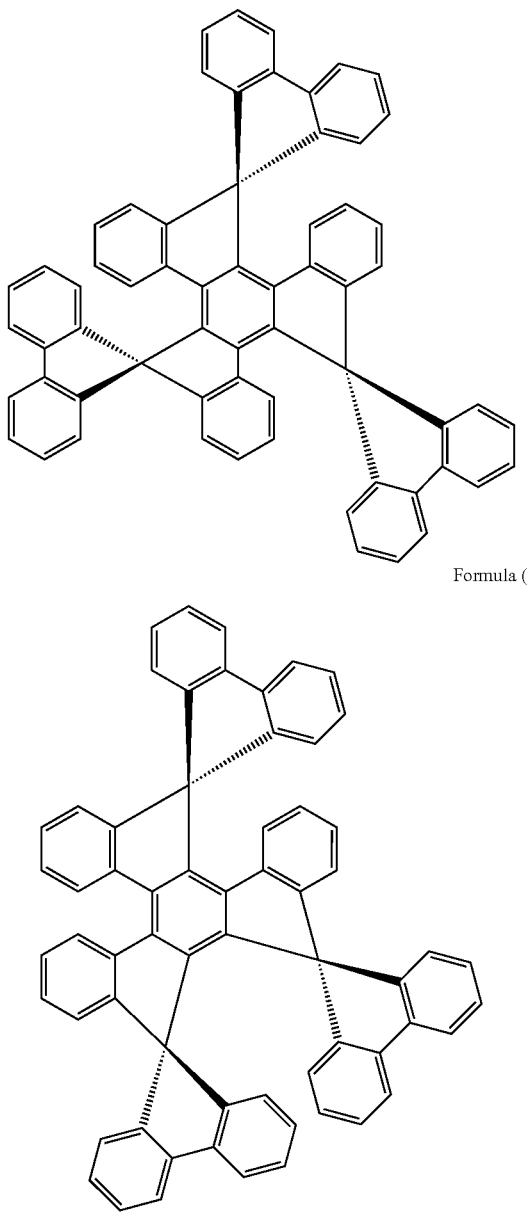

and derivatives and salts thereof.

6. The compound of claim 1, wherein said compounds have a three-fold axis of rotation.

7. The compound of claim 1, wherein said compounds contain at least one R containing at least one aromatic ring system containing at least one condensed aryl or heteroaryl group, which is optionally substituted or unsubstituted.

8. The compound of claim 1, wherein said compounds contain at least one R containing at least one carbonyl group, phosphine group, phosphine oxide group, thio group, sulfoxide group, or sulfone group; and/or at least one R and/or $R^1$ that contains at least one carbazole group.

9. The compound of claim 1, wherein said compounds contain at least one R containing at least one arylamine unit, diarylamine unit, carbazole unit, triarylamine unit, diarylphosphine unit, triarylphosphine unit, and/or thiophene derivative.

10. The compound of claim 1, wherein said compounds contain
at least one R and/or $R^1$ containing at least one electron-deficient heteroaryl group; and/or
at least one R and/or $R^1$ containing a carbonyl group, phosphine group, sulfoxide group, and/or sulfone group; and/or
at least one R and/or $R^1$ containing at least one substituted or unsubstituted oligophenylene group.

11. The compound of claim 1, wherein said compounds contain at least one R and/or $R^1$ containing at least one vinylaryl unit, stilbene unit, and/or tolan unit.

12. An oligomer, polymer or dendrimer comprising recurring units of the compound of claim 1.

13. An organic electronic device comprising at least one organic layer which comprises at least one compound of claim 1.

14. The organic electronic device of claim 13 wherein said organic electronic device is selected from the group consisting of organic and polymeric light-emitting diodes, organic field-effect transistors, organic thin-film transistors, organic light-emitting transistors, organic integrated circuits, organic solar cells, organic field-quench devices, light-emitting electro-chemical cells, and organic laser diodes.

15. The organic electronic device of claim 13 wherein said organic electronic device is an organic and polymeric light-emitting diode.

16. An organic electroluminescent device comprising at least one organic layer which comprises at least one compound of claim 1, wherein at least one of said at least one organic layer is an emission layer; an anode; a cathode; and one or more additional organic layers selected from the group consisting of hole-injection layers, hole-transport layers, hole-blocking layers, electron-transport layers, electron-injection layer, and combinations thereof.

17. The organic electroluminescent device of claim 16, wherein said emission layer is a fluorescent or phosphorescent emission layer.

18. The organic electroluminescent device of claim 16, further comprising a fluorescent dopant selected from the group consisting of monostyrylamines, distyrylamines, tristyrylamines, tetrastyrylamines, and arylamines.

19. The organic electroluminescent device of claim 16, further comprising a phosphorescent dopant comprising metal complexes containing at least one element having an atomic number of greater than 20 and less than 84.

20. The organic electroluminescent device of claim 19, wherein said at least one element has an atomic number of greater than 38 and less than 84.

21. A fluorescent organic electroluminescent device comprising an emission layer which comprises a host material and a fluorescent dopant comprising at least one compound according to claim 1.

22. The fluorescent organic electroluminescent device of claim 21, wherein said host material is selected from the group consisting of oligoarylenes, oligoarylenevinylenes, polypodal metal complexes, hole-conducting compounds, and electron-conducting compounds.

* * * * *